US010519476B2

(12) United States Patent
Kurihara et al.

(10) Patent No.: US 10,519,476 B2
(45) Date of Patent: Dec. 31, 2019

(54) METHOD OF PRODUCING SUGAR LIQUID

(71) Applicant: Toray Industries, Inc., Tokyo (JP)

(72) Inventors: Hiroyuki Kurihara, Kamakura (JP);
Hiroko Ishizuka, Kamakura (JP);
Atsushi Minamino, Kamakura (JP);
Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 523 days.

(21) Appl. No.: 14/401,900

(22) PCT Filed: May 17, 2013

(86) PCT No.: PCT/JP2013/063771
§ 371 (c)(1),
(2) Date: Nov. 18, 2014

(87) PCT Pub. No.: WO2013/172446
PCT Pub. Date: Nov. 21, 2013

(65) Prior Publication Data
US 2015/0125908 A1  May 7, 2015

(30) Foreign Application Priority Data

May 18, 2012 (JP) ................. 2012-114234

(51) Int. Cl.
| C12P 19/14 | (2006.01) |
| C12M 1/00 | (2006.01) |
| C12P 7/56 | (2006.01) |
| C13K 1/02 | (2006.01) |
| C13K 13/00 | (2006.01) |
| C12P 19/02 | (2006.01) |
| C12N 9/42 | (2006.01) |
| C12M 1/40 | (2006.01) |
| C12P 7/14 | (2006.01) |
| C12P 7/10 | (2006.01) |

(52) U.S. Cl.
CPC ............ *C12P 19/14* (2013.01); *C12M 21/18* (2013.01); *C12M 45/06* (2013.01); *C12M 45/09* (2013.01); *C12M 45/20* (2013.01); *C12M 47/10* (2013.01); *C12N 9/2437* (2013.01); *C12P 7/10* (2013.01); *C12P 7/14* (2013.01); *C12P 7/56* (2013.01); *C12P 19/02* (2013.01); *C13K 1/02* (2013.01); *C13K 13/002* (2013.01); *C12P 2201/00* (2013.01); *Y02E 50/16* (2013.01)

(58) Field of Classification Search
None
See application file for complete search history.

(56) References Cited

U.S. PATENT DOCUMENTS 9,212,377 B2 * 12/2015 Kurihara ............... C13K 1/02
9,624,516 B2 *  4/2017 Kurihara ............... C12P 19/00

2012/0009626 A1 *  1/2012 Suzuki ................. C12M 21/12
  435/72
2012/0058544 A1 *  3/2012 Genta ..................... B08B 1/04
  435/262
2014/0017736 A1 *  1/2014 Kurihara ................ C12P 19/02
  435/99
2014/0342444 A1 * 11/2014 Minamino ............. B01D 61/58
  435/294.1

FOREIGN PATENT DOCUMENTS

| JP | 63-087994 A | 4/1988 | |
| JP | 2006-087319 A | 4/2006 | |
| JP | 2008-206484 A | 9/2008 | |
| JP | 2009-183805 A | 8/2009 | |
| JP | 2010-036058 A | 2/2010 | |
| JP | 2011-223975 A | 11/2011 | |
| JP | 6387994 B2 * | 9/2018 | |
| WO | WO 2008073186 A2 * | 6/2008 | ............... C08H 8/00 |
| WO | 2010/067785 A1 | 6/2010 | |
| WO | 2011/115039 A1 | 9/2011 | |
| WO | 2011/115040 A1 | 9/2011 | |
| WO | 2011/162009 A1 | 12/2011 | |

OTHER PUBLICATIONS

Liu, Shijie et al. Membrane Filtration: Concentration and Purification of Hydrolyzates from Biomass. Journal of Biobased Materials and Bioenergy. vol. 2, 121-134. 2008.*
Supplementary European Search Report dated May 18, 2016, of corresponding European Application No. 13791282.0.
Partial Supplementary European Search Report dated Jan. 29, 2016 from corresponding European Patent Application No. 13791282.0.
Xu, J. et al.: "A Novel Stepwise Recovery Strategy of Cellulase Adsorbed to the Residual Substrate after Hydrolysis of Steam Exploded Wheat Straw," *Applied Biochemistry and Biotechnology*, Oct. 2007, vol. 143, No. 1, pp. 93-100.
Dekker, R.F.H.: "Application of a Magnetic Immobilized ß-Glucosidase in the Enzymatic Saccharification of Steam-Exploded Lignocellulosic Residues," *Applied Biochemistry and Biotechnology*, Jan. 1990, vol. 23, No. 1, pp. 25-39.

(Continued)

*Primary Examiner* — Nghi V Nguyen
(74) *Attorney, Agent, or Firm* — DLA Piper LLP (US)

(57) ABSTRACT

A method of producing a sugar liquid from cellulose-containing biomass includes (1) to (3): (1): subjecting a cellulose-containing biomass to hydrothermal treatment and thereafter separating the treated cellulose-containing biomass into a hydrothermally-treated liquid and a cellulose-containing solid content; (2): adding a filamentous fungus-derived cellulase to the cellulose-containing solid content obtained in (1) to hydrolyze the cellulose and thereafter separating the hydrolysate into a saccharification residue and a sugar liquid; and (3): washing the saccharification residue obtained in (2) with the hydrothermally-treated liquid obtained in (1) to elute the filamentous fungus-derived cellulase adsorbed to the saccharification residue into the hydrothermally-treated liquid and thereafter obtaining a solution component comprising the filamentous fungus-derived cellulase by solid-liquid separation.

10 Claims, 6 Drawing Sheets

(56) References Cited

OTHER PUBLICATIONS

Deshpande, M. V. et al.: "Reutilization of Enzymes for Saccharification of Lignocellulosic Materials," *Enzyme and Microb. Technology*, Aug. 1, 1984, vol. 6, No. 8, pp. 338-340.

Sinitsyn, A. P. et al.: "Recovery of Enzymes from the Insoluble Residue of Hydrolyzed Wood," *Applied Biochemistry and Biotechnology*, 1983, vol. 8, pp. 25-29.

Nonaka, H. et al., "Adsorption Recovery of Cellulose Using Lignophenol," *The Japan Institute of Energy Taikai Koen Yoshishu*, Jul. 30, 2009, vol. 18, pp. 182-183.

Kobayashi, A. et al., "Lignophenol ni yoru Cellulase no Kyuchaku Kaishu to Sairiyo," *The Society of Polymer Science*, May 10, 2011, vol. 60, No. 1, pp. 2090-2091.

Notification of Reasons for Refusal dated May 19, 2017, of corresponding Japanese Application No. 2013-535975, along with an English translation.

\* cited by examiner

METHOD OF PRODUCING SUGAR LIQUID

TECHNICAL FIELD

This disclosure relates to method of producing a sugar liquid from cellulose-containing biomass.

BACKGROUND

Recently, methods of producing a sugar liquid have been widely examined, which methods comprise a pretreatment of cellulose-containing biomass by an acid treatment, a hydrothermal treatment, an alkali treatment, or the like, followed by addition of filamentous fungus-derived cellulase for hydrolysis. However, as a drawback of such methods using filamentous fungus-derived cellulases, there is a problem in that the production cost of the sugar liquid increase due to a large amount of saccharification enzyme used and the a high price thereof.

As a technique to solve this problem, methods have been proposed, wherein filamentous fungus-derived cellulase used in cellulose hydrolysis is recovered and reused. Examples of what have been disclosed include a method comprising performing continuous solid-liquid separation by a spin filter, filtering a sugar liquid obtained by the separation through an ultrafiltration membrane, and recovering filamentous fungus-derived cellulase (Japanese Patent Application Laid-Open Publication No. 2006-87319); a method comprising adding a surfactant at the stage of enzymatic saccharification to inhibit adsorption of filamentous fungus-derived cellulase and thereby improve a recovery efficiency (Japanese Patent Application Laid-Open Publication No. 63-87994); a method comprising subjecting residues after enzymatic saccharification to electric treatment to recover filamentous fungus-derived cellulase component (Japanese Patent Application Laid-Open Publication No. 2008-206484); a method comprising performing a secondary hydrolysis of the saccharification residue to thereby increase the recovery amount of adsorbed enzyme (WO 2011/115039); and a method comprising performing a primary hydrolysis by first adding recovered cellulase and subsequently performing a secondary hydrolysis repeatedly by adding unused cellulase to increase the amount of enzyme recovered and the amount of sugars generated (WO 2011/115040). However, those methods have failed to reach fundamental solutions to the problem.

When hydrothermal treatment was employed as pretreatment when a sugar liquid was produced from cellulose-containing biomass, a large amount of hydrothermally-treated liquid was discharged when cellulose was hydrolyzed by using filamentous fungus cellulase after the hydrothermal treatment of the cellulose-containing biomass, which hydrothermally-treated liquid contained diluted oligosaccharides and enzymatic saccharification inhibitors such as furan-based compounds and aromatic compounds.

In view of this, it could be helpful to find a means of utilizing the hydrothermally-treated liquid which has been dealt with as a waste liquid at the time of the saccharification process of the cellulose-containing biomass and to reduce the amount of enzyme used in the hydrolysis of the cellulose-containing solid content.

SUMMARY

We found that a hydrothermally-treated liquid obtained by a hydrothermal treatment of cellulose-containing biomass can be used as an elutant to recover filamentous fungus-derived cellulases for cellulose hydrolysis from a saccharification process.

We thus provide:

[1] A method of producing a sugar liquid from cellulose-containing biomass, the method comprising the following steps (1) to (3):

step (1): the step of subjecting a cellulose-containing biomass to hydrothermal treatment and thereafter separating the treated cellulose-containing biomass into a hydrothermally-treated liquid and a cellulose-containing solid content;

step (2): the step of adding a filamentous fungus-derived cellulase to the cellulose-containing solid content obtained in the step (1) to hydrolyze the cellulose and thereafter separating the hydrolysate into a saccharification residue and a sugar liquid; and step (3): the step of washing the saccharification residue obtained in the step (2) with the hydrothermally-treated liquid obtained in the step (1) to elute the filamentous fungus-derived cellulase adsorbed to the saccharification residue into the hydrothermally-treated liquid and thereafter obtaining a solution component comprising the filamentous fungus-derived cellulase by solid-liquid separation.

[2] The method of producing a sugar liquid according to [1] comprising the step (4) of filtering the solution component obtained in the step (3) through an ultrafiltration membrane to thereby recover the filamentous fungus-derived cellulase as a retentate and at the same time obtain a sugar liquid as a permeate.

[3] The method of producing a sugar liquid according to [2], wherein the filamentous fungus-derived cellulase recovered in the step (4) is reused in the cellulose hydrolysis in the step (2).

[4] The method of producing a sugar liquid according to any of [1] to [3], wherein the filamentous fungus-derived cellulase is cellulase derived from *Trichoderma*.

[5] The method of producing a sugar liquid according to any of [1] to [4], wherein the hydrothermal treatment of the step (1) is a treatment within a temperature range of 120 to 240° C.

[6] The method of producing a sugar liquid according to any of [1] to [5], wherein the hydrothermally-treated liquid used in the step (3) comprises 1 g/L or more of an inorganic ion, acetic acid and/or furfural in total.

[7] The method of producing a sugar liquid according to any of [1] to [6], wherein the saccharification residue is washed with a hydrothermally-treated liquid at 30 to 70° C. in the step (3).

[8] The method of producing a sugar liquid according to any of [1] to [7], wherein the step (2) comprises separating the hydrolysate into a saccharification residue and a sugar liquid by membrane separation, and the step (3) comprises washing the saccharification residue by passing the hydrothermally-treated liquid through the saccharification residue on the surface of the membrane in a vertical direction to obtain a solution component comprising the filamentous fungus-derived cellulase.

[9] The method of producing a sugar liquid according to [8], wherein the membrane separation is press filtration or membrane separation by a belt filter.

[10] A method of producing a chemical substance comprising the step of producing the sugar liquid by the method according to any of [1] to [9] and the step of culturing a microorganism capable of producing a chemical substance using the sugar liquid as a fermentation raw material.

[11] An apparatus that produces a sugar liquid comprising: a hydrothermal treatment apparatus for hydrothermal treatment of cellulose-containing biomass and solid-liquid separation of a hydrothermally treated product; a hydrolysis apparatus for hydrolysis of a cellulose-containing solid content discharged from the hydrothermal treatment apparatus by filamentous fungus-derived cellulase; a sugar liquid recovery apparatus for solid-liquid separation of a hydrolysate of the cellulose-containing solid content obtained in the hydrolysis apparatus; and an enzyme recovery apparatus for mixture, thermal retention and solid-liquid separation of a saccharification residue separated in the sugar liquid recovery apparatus and a hydrothermally-treated liquid discharged from the hydrothermal treatment apparatus.

[12] The apparatus of producing a sugar liquid according to [11], wherein the sugar liquid recovery apparatus and the enzyme recovery apparatus are an integrated apparatus.

[13] The apparatus of producing a sugar liquid according to [12], wherein the integrated apparatus of the sugar liquid recovery apparatus and the enzyme recovery apparatus is a press filtration apparatus or a belt filtration apparatus.

[14] The apparatus of producing a sugar liquid according to [13], wherein the membrane separation apparatus is a press filtration apparatus or a belt filtration apparatus.

[15] The apparatus of producing a sugar liquid according to any of [11] to [14], wherein the enzyme recovery apparatus comprises an ultrafiltration membrane separation apparatus for separating the mixture into the filamentous fungus-derived cellulases and the sugar liquid.

The amount of enzyme recovered and activity of filamentous fungus-derived cellulose adsorbed to an enzymatic saccharification residue can be improved by virtue of an effect of a biomass extract component contained in a hydrothermally-treated liquid, thereby reducing the amount of enzyme used in the step of producing a sugar liquid with cellulose-containing biomass as a raw material. In addition, by eluting filamentous fungus-derived cellulases adsorbed in the enzymatic saccharification residue with the hydrothermally-treated liquid to recover the filamentous fungus-derived cellulose, the saccharification of oligosaccharides contained in the hydrothermally-treated liquid also becomes feasible, thereby increasing the sugar yield of the whole production process.

DESCRIPTION OF SYMBOLS

Figure 1:
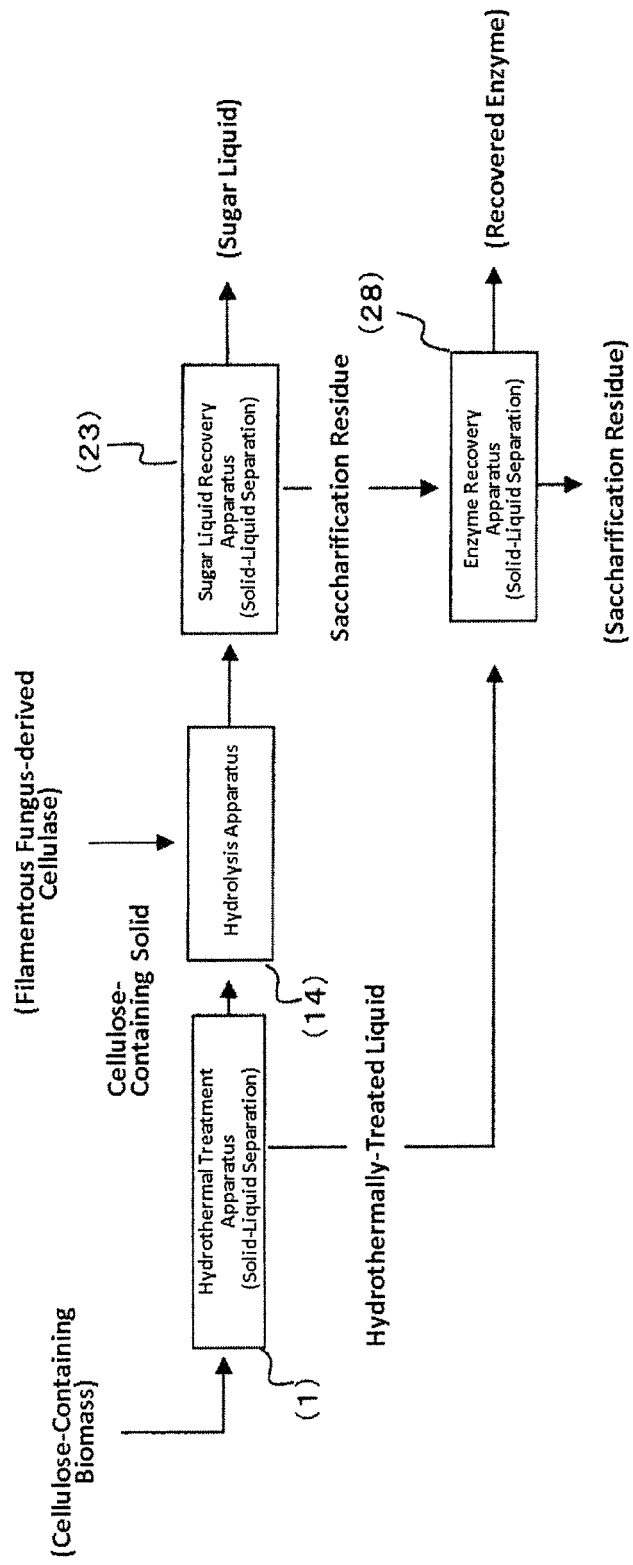
FIG. 1 is a drawing showing a block flow of the method of producing a sugar liquid.

1 Hydrothermal treatment apparatus
2 Thermal retention pressurized vessel
3 Heater
4 Raw material feeder
5 Stirring apparatus
6 Transfer apparatus
7 Pressure release tank
8 Water dilution tank
9 Pump
10 Solid-liquid separator
11 Separation membrane
12 Valve
13 Belt conveyor
14 Hydrolysis apparatus
15 Kneader
16 Stirring liquid transfer apparatus
17 Heater
18 Stirring apparatus
19 Stirring tank
20 Heater
21 Valve
22 Pump
23 Sugar liquid recovery apparatus
24 Solid-liquid separator
25 Separation membrane
26 Valve
27 Belt conveyor
28 Enzyme recovery apparatus
29 Heat exchanger
30 Thermal retention apparatus
31 Thermal retention tank
32 Stirring apparatus
33 Valve
34 Pump
35 Solid-liquid separator
36 Separation membrane
37 Washing liquid tank
38 Valve
39 Belt conveyor
40 Ultrafiltration membrane apparatus
41 Sugar liquid storage tank
42 Microfiltration membrane pump
43 Microfiltration membrane module
44 Microfiltration membrane filtrate tank
45 Ultrafiltration membrane pump
46 Ultrafiltration membrane module
47 Pump
48 Membrane separation apparatus
49 Membrane
50 Hydrolysate supply line
51 Recovery line
52 Hydrothermally-treated liquid supply line

DETAILED DESCRIPTION

Modes of carrying out our methods will be described in detail for each step.

Step (1) The step of subjecting a cellulose-containing biomass to hydrothermal treatment and thereafter separating the treated cellulose-containing biomass into a hydrothermally-treated liquid and a cellulose-containing solid content:

Cellulose-containing biomass refers to herbaceous biomass such as bagasse, switchgrass, napier grass, *Erianthus*, corn stover, corncob, rice straw, wheat straw, or coconut shells, or wood-base biomass such as trees, poplar, or waste building materials; and further refers to biomass derived from aquatic environment such as seaweeds or sea grass. Such a biomass contains, in addition to cellulose and hemicellulose (hereinafter, referred to as "cellulose" as a general term of cellulose and hemicellulose), lignin which is an aromatic polymer, and the like.

In this step, for the purpose of improving the efficiency of enzymatic saccharification in the step 2 described later, a hydrothermal treatment of cellulose-containing biomass is carried out. The hydrothermal treatment hydrolyzes hemicellulose present in the cellulose-containing biomass and promotes solubilization of lignin to put cellulose and hemicellulose into a state of being susceptible to enzymatic hydrolysis by adding water such that the solids content of the cellulose-containing biomass comes to be 0.1 to 50% by weight and subjecting the cellulose-containing biomass to the hydrothermal treatment at a temperature of 100 to 400° C. and for from one second to 60 minutes. It is to be noted that a reaction temperature of the hydrothermal treatment in this step is not particularly restricted, only need to be set as appropriate to an optimum temperature that leads to the high efficiency of enzymatic saccharification according to the kind of cellulose-containing biomass. It is usually 120° C. to 240° C. and preferably 180° C. to 240° C. Further, an acid such as sulfuric acid, hydrochloric acid, or acetic acid, or an alkali such as sodium hydroxide or calcium hydroxide may be added in the hydrothermal treatment. Yet the addition amount thereof is preferably kept to the minimum; and the final concentration is preferably less than 2% by weight upon carrying out the hydrothermal treatment, and further preferably less than 1% by weight. It is to be noted that when the acid or alkali is added at the time of the hydrothermal treatment, the acid or alkali is preferably neutralized at a stage prior to addition of a saccharification enzyme or hydrolysis described later. The addition of the acid or alkali at the time of the hydrothermal treatment enables the hydrothermal treatment to be carried out in a lower temperature condition.

The number of times that the hydrothermal treatment is carried out is not particularly limited and the hydrothermal treatment only need to be carried out once or more. Further, when the hydrothermal treatment is carried out twice or more, the second or later hydrothermal treatment may be carried out in a condition setting different from that of the first treatment.

In this step, a hydrothermally-treated liquid and a cellulose-containing solid content are separated after the hydrothermal treatment. When the cellulose-containing biomass is subjected to the hydrothermal treatment, low-molecular compounds that inhibit enzymatic saccharification such as furfural, HMF, vanillin, guaiacyl alcohol, syringic acid, coumaric acid, ferulic acid, acetic acid, formic acid, or inorganic ions are generated as byproducts (hereinafter, these are collectively referred to as enzymatic saccharification inhibitors); and the enzymatic saccharification inhibitor can be separated in a hydrothermally-treated liquid side by solid-liquid separation of the hydrothermally-treated product into the hydrothermally-treated liquid and the cellulose-containing solid content. As for a technique of solid-liquid separation, press filtration, belt filter, Pneumapress, screw press, centrifugation, screw decanter, or the like can be used; and further in cases where a separation function such as screw press is present inside a hydrothermal treatment apparatus, the separation into the hydrothermally-treated liquid and the cellulose-containing solid content is feasible in the process of that hydrothermal treatment. Further, the enzymatic saccharification inhibitor can be more thoroughly removed by washing the cellulose-containing solid content with water or the like. After the hydrothermal treatment, the cellulose-containing solid content obtained by the solid-liquid separation may be subjected to an alkali treatment, an acid treatment, or the like.

Step (2) The step of adding filamentous fungus-derived cellulase to the cellulose-containing solid content obtained by the solid-liquid separation in the step (1) to hydrolyze the cellulose and thereafter separating into a saccharification residue which contains the filamentous fungus-derived cellulases and a sugar liquid:

In the step (2), filamentous fungus-derived cellulases are added to the cellulose-containing solid content obtained by the solid-liquid separation in the step (1) to hydrolyze the cellulose and then to separate into a saccharification residue and a sugar liquid.

The filamentous fungus-derived cellulases for use in this step comprises a group of cellulase enzymes capable of hydrolyzing a sugar polymer with glucose being linked by β1-4 bond such as cellobiohydrolase, endoglucanase, exoglucanase, or β glucosidase; and a group of hemicellulase enzymes capable of hydrolyzing a sugar polymer with xylose being linked by β1-4 bond such as xylanase or xylosidase.

Cellobiohydrolase is a general term for cellulases characterized by hydrolyzing cellulose from the terminal portion. The group of enzymes belonging to cellobiohydrolase is described as the EC number: EC3.2.1.91.

Endoglucanase is a general term for cellulases characterized by hydrolyzing cellulose molecular chains from their middle portion. The group of enzymes belonging to exoglucanase is described as the EC numbers: EC3.2.1.4, EC3.2.1.6, EC3.2.1.39, and EC3.2.1.73.

Exoglucanase is a general term for cellulases characterized by hydrolyzing cellulose molecular chains from their termini. The group of enzymes belonging to exoglucanase is described as the EC numbers: EC3.2.1.74 and EC3.2.1.58.

β-glucosidase is a general term for cellulases characterized by acting on cello oligosaccharides or cellobiose. The group of enzymes belonging to β-glucosidase is described as the EC number: EC3.2.1.21.

Xylanase is a general term for cellulases characterized by acting on hemicellulose or, in particular, xylan. The group of enzymes belonging to xylanase is described as the EC number: EC3.2.0.1.8.

Xylosidase is a general term for cellulases characterized by acting on xylooligosaccharides. The group of enzymes belonging to xylosidase is described as the EC number: EC3.2.1.37.

Further, the filamentous fungus-derived cellulases may include other enzyme components that are involved in biomass degradation other than the above. Examples of other enzyme components include mannanase, mannosidase, arabinofuranosidase, xylan esterase, ferulic acid esterase, and chitinase. As the saccharification enzyme, one having a high specific activity for the hydrolysis of the cellulose-containing solid content can preferably be used.

As the filamentous fungus-derived cellulases, what can be used is cellulase derived from the genus *Trichoderma*, the genus *Aspergillus*, the genus *Cellulomonas*, the genus *Clostridium*, the genus *Streptomyces*, the genus *Humicola*, the genus *Acremonium*, the genus *Irpex*, the genus *Mucor*, the genus *Talaromyces*, the genus *Phanerochaete*, white rot fungi, brown rot fungi, or the like. It is preferred to use, of these cellulases derived from the filamentous fungus, filamentous fungus-derived cellulases derived from *Trichoderma* which has a high cellulose degrading activity.

Further, the genus *Trichoderma* microorganism is not particularly restricted; and concrete examples thereof can include *Trichoderma reesei* QM9414, *Trichoderma reesei* QM9123, *Trichoderma reesei* RutC-30, *Trichoderma reesei* PC3-7, *Trichoderma reesei* ATCC68589, *Trichoderma reesei* CL-847, *Trichoderma reesei* MCG77, *Trichoderma reesei* MCG80, and *Trichoderma viride* QM9123. Also may be used is a mutant strain which is a microorganism derived from the genus *Trichoderma* described earlier and is obtained by subjecting the microorganism to a mutation treatment with a mutagen or UV irradiation, or the like to improve the productivity of saccharification enzymes.

As the cellulase derived from *Trichoderma*, crude enzymes are preferably used. The crude enzyme is derived from a culture supernatant obtained by culturing a microorganism of the genus *Trichoderma* in an optional period of time in a culture medium prepared such that the microorganism produces saccharification enzymes. Medium components to be used are not particularly restricted and a culture medium to which cellulose or xylan is added for the purpose of promoting the generation of cellulase can be used in general. And, as the crude enzyme, a culture liquid as is or a supernatant of the culture obtained only by removing bacterial cells is preferably used.

The microorganism of the genus *Trichoderma* produces a strong cellulase component in a culture liquid. When it comes to β glucosidase, because it retains β glucosidase activity intracellularly or on the cell surface layer, the β glucosidase activity is low in the culture liquid. Thus, β glucosidase from different species or the same species may be further added to the crude enzyme. As the β glucosidase from different species, β glucosidase derived from the genus *Aspergillus* can be preferably used. Examples of the β glucosidase derived from the genus *Aspergillus* include Novozyme188 which is commercially available from Novozymes A/S. As a method of adding the β glucosidase from different species or the same species to the crude enzyme, a method comprising introducing a gene to the microorganism of the genus *Trichoderma*, culturing the microorganism of the genus *Trichoderma* subjected to gene recombination to produce β glucosidase in a culture liquid, and isolating the culture liquid may be also employed.

The temperature for a hydrolysis reaction by filamentous fungus-derived cellulase is preferably 15 to 100° C., more preferably 40 to 60° C., and most preferably 50° C. Further, the pH at the time of the hydrolysis reaction is preferably pH 3 to 9, more preferably pH 4 to 5.5, and most preferably pH 5. For pH adjustment, an acid or alkali can be added to adjust to an intended pH and further a buffer may be used as appropriate. Besides, it is preferred to carry out stirring and mixing during the hydrolysis of the cellulose-containing solid content to attain a homogeneous sugar concentration in the hydrolysate for the purpose of promoting contact with cellulase and hemicellulase. The solid concentration of pretreated cellulose product is preferably 1 to 25% by weight.

Further, in this step, the hydrolysate by filamentous fungus-derived cellulase is separated into saccharification residues and a sugar liquid which is an intended product. The solid-liquid separation of the hydrolysate can be carried out by a known technique for solid-liquid separation. Preferred is solid-liquid separation by membrane separation; and more preferred is solid-liquid separation by press filtration or belt filter whereby solid contents or suspended components contained in the separated hydrothermally-treated liquid can be relatively reduced. Such a solid-liquid separation may be carried out by combining one or more techniques; and it is not restricted as long as it is a means capable of efficiently recovering the saccharification residue including the filamentous fungus-derived cellulase.

It is to be noted that even though the majority of filamentous fungus-derived cellulases are adsorbed to the saccharification residue, a small amount thereof remains in the sugar liquid, and thus that the step of recovering the saccharification enzyme from the sugar liquid may be added. In that case, if the sugar liquid is further subjected to membrane filtration by a microfiltration membrane after the first solid-liquid separation by a filtration method such as centrifugation method or press filtration to further remove solids, fouling of the ultrafiltration membrane can be inhibited when filamentous fungus-derived cellulase is recovered from the sugar liquid by an ultrafiltration membrane described later.

Step (3) The step of washing the saccharification residue obtained in the step (2) with the hydrothermally-treated liquid obtained in the step (1) to elute the filamentous fungus-derived cellulase adsorbed to the saccharification residue into the hydrothermally-treated liquid and thereafter obtaining a solution component comprising the filamentous fungus-derived cellulase by solid-liquid separation:

In the step (3), the filamentous fungus-derived cellulase adsorbed to (bound to) the saccharification residue is eluted (desorbed) to the hydrothermally-treated liquid with utilizing biomass extract components contained in the hydrothermally-treated liquid by washing the saccharification residue with the hydrothermally-treated liquid. In the meantime, due to an effect by components other than sugars contained in the hydrothermally-treated liquid, the desorption of cellulase and hemicellulase adsorbed to the saccharification residue to the hydrothermally-treated liquid is promoted. That's because the concentration of inorganic ions, acetic acid, and/or furfural contained in the hydrothermally-treated liquid is higher, the effect of desorbing the filamentous fungus-derived cellulase adsorbed to the saccharification residue is higher. It is preferred that the hydrothermally-treated liquid in the step (3) contains inorganic ions, acetic acids, and/or furfural in 1 g/L or more in total. In addition, as another effect of washing the saccharification residue with the hydrothermally-treated liquid, oligosaccharides contained in the hydrothermally-treated liquid are hydrolyzed by the action of filamentous fungus-derived cellulase adsorbed in the saccharification residue. The amount of xylose mainly increases by the hydrolysis of the hydrothermally-treated liquid.

As for washing the saccharification residue, it is preferred to wash with a hydrothermally-treated liquid at 30 to 70° C. That's because the use of the hydrothermally-treated liquid at 30 to 70° C. produces an effect of promoting the desorption of enzyme components adsorbed to the saccharification residue and further an effect of hydrolyzing oligosaccharides contained in the hydrothermally-treated liquid by the action of the enzyme component adsorbed to the saccharification residue as described adobe. It is to be noted that the more preferred temperature of the hydrothermally-treated liquid is 40 to 60° C.

As for the solid-liquid separation in the step (3), a known solid-liquid separation can be used; and similarly to that of the above-mentioned step (2), preferred is solid-liquid separation by membrane separation is preferred and more preferred is press filtration or belt filter. In particular, when the steps (2) and (3) involve solid-liquid separation by membrane separation, the solid-liquid separation into a saccharification residue and a sugar liquid by membrane separation is carried out in the step (2) and thereafter, by passing the hydrothermally-treated liquid through the saccharification residue on the membrane surface, the washing of the saccharification residue by the hydrothermally-treated liquid and solid-liquid separation can be carried out, which thereby enables the steps (2) and (3) to be carried out in the same apparatus.

As for passing the hydrothermally-treated liquid through the saccharification residue, it is preferred to pass the hydrothermally-treated liquid through the saccharification residue on the membrane surface in a vertically direction, which can thereby generate a rapid flow of the hydrothermally-treated liquid in the saccharification residue, enabling more enzyme components adsorbed in the saccharification residue to be recovered. Further, it is preferred to circulate and pass again one that once passed the saccharification residue, thereby enabling still more enzyme components to be recovered.

The washing liquid used in the step (3) is subjected to solid-liquid separation and the solution component is filtered through an ultrafiltration membrane. As a retentate, the filamentous fungus-derived cellulase can be separated, recovered, and further concentrated ion (step (4)). In the meantime, a sugar liquid can be obtained as a permeate of the ultrafiltration membrane. The solid-liquid separation in the step 3 can be carried out by a known technique for solid-liquid separation such as a centrifugation method such as screw decanter, a filtration method such as pressure suction filtration, or membrane filtration method such as microfiltration. Such a solid-liquid separation may be carried out by combining one or more techniques; and it is not restricted as long as it is a means capable of efficiently removing the saccharification residue. Note that, from the viewpoint of inhibiting the fouling of an ultrafiltration membrane described later, it is preferred that the solution component after the solid-liquid separation contains as few solids as possible. In particular, it is preferred that, after the first solid-liquid separation by a centrifugation method or a filtration method such as press filtration, the solution component thus obtained is further subjected to membrane filtration with a microfiltration membrane to completely remove the solid. The microfiltration membrane is referred to also as membrane filtration and is a separation membrane capable of separating and removing particles of about 0.01 to 10 µm from a fine particle suspension using pressure difference as a driving force. The microfiltration membrane has fine pores ranging from 0.01 to 10 µm on the surface thereof and fine particle components that are larger than the fine pore can be separated and removed in the membrane side. Examples of materials of the microfiltration membrane include cellulose acetate, aromatic polyamide, polyvinyl alcohol, polysulfone, polyvinylidene fluoride, polyethylene, polyacrylonitrile, ceramic, polypropylene, polycarbonate, and polytetrafluoroethylene (Teflon (registered trademark)); and it is not particularly restricted and a microfiltration membrane made of polyvinylidene fluoride is preferred in view of antifouling properties, chemical resistance, strength, and filtration properties.

Subsequently, the above-mentioned solution component obtained by solid-liquid separation is subjected to an ultrafiltration membrane treatment. An ultrafiltration membrane refers to a separation membrane that has in general a fine pore size of 1.5 to 250 nanometers and is capable of blocking water-soluble polymers with a molecular weight of 1,000 to 200,000 as a retentate. The ultrafiltration membrane need only to have a molecular weight cut off that allows for the recovery of filamentous fungus-derived cellulase; and the preferred molecular weight cut off is 1,000 to 100,000 Da and more preferably 10,000 to 30,000 Da. As for a material of the ultrafiltration membrane, a membrane made of materials such as polyether sulfone (PES), polyvinylidene difluoride (PVDF), or regenerated cellulose can be used; and it is preferred to use an ultrafiltration membrane with a synthetic polymer such as PES or PVDF as a material because cellulose undergoes degradation by cellulase. As for the shape of the ultrafiltration membrane, a tubular system, a spiral element, a flat sheet membrane, or the like can be preferably used. Examples of the ultrafiltration membrane filtration include a cross flow system or a dead end filtration system; and the cross flow filtration system is preferred in terms of the fouling or flux.

It is to be noted that the filamentous fungus-derived cellulase separated and recovered by the ultrafiltration membrane can be reused in the cellulose-containing solid of the step 2. Upon the reuse, a cellulase or hemicellulase that has not been used may be added and used in conjunction with the recovered enzyme and also enzyme components other than these may be separately added.

Step of Concentrating Sugars

The sugar liquid obtained by the method of producing a sugar liquid can be further subjected to filtration through a nanofiltration membrane and/or a reverse osmosis membrane, which is a method described in WO 2010/067785 to thereby yield, as a retentate, a concentrated sugar liquid in which the sugar component is concentration.

The nanofiltration membrane is a membrane that is also called a nanofilter (nanofiltration membrane, NF membrane) and is in general defined as a "membrane permeating monovalent ions whereas blocking divalent ions." It is a membrane that is thought to have microscopic openings of about several nanometers and mainly used for blocking fine particles or molecules, ions, salts, or the like in water.

The reverse osmosis membrane is a membrane that is also called an RO membrane and is in general defined as a "membrane having a function of removing salts including monovalent ions." The membrane is a membrane that is thought to have microscopic openings ranging from about several angstroms to several nanometers and mainly used for removing ion components, for example, in desalination of sea water or production of ultrapure water.

As materials of the nanofiltration membrane or reverse osmosis membrane, polymer materials such as cellulose acetate-based polymers, polyamide, polyester, polyimide, vinyl polymers, or polysulfone can be used; and the membrane is not limited to be a membrane composed of one kind of the above-mentioned material and may be a membrane containing plural membrane materials.

As the nanofiltration membrane, a spiral-type membrane element is preferably used. Concrete examples of preferred nanofiltration membrane elements include GEsepa manufactured by GE Osmonics, which is a cellulose acetate-based nanofiltration membrane element; NF99 or NF99HF manufactured by Alfa Laval, which is a nanofiltration membrane element with polyamide as a functional layer; NF-45, NF-90, NF-200, NF-270, or NF-400 manufactured by Filmtec, which is a nanofiltration membrane element with cross-linked piperazine polyamide as a functional layer; and SU-210, SU-220, SU-600, or SU-610 manufactured by Toray Industries, Inc. which is a nanofiltration membrane element containing a nanofiltration membrane UTC60 manufactured by the same company with cross-linked piperazine polyamide as a major component. More preferred is NF99 or NF99HF; NF-45, NF-90, NF-200, or NF-400; or SU-210, SU-220, SU-600, or SU-610; and still more preferred is SU-210, SU-220, SU-600, or SU-610.

Examples of materials of the reverse osmosis membrane include composite membranes with a cellulose acetate-based polymer as a functional layer (hereinafter referred to as cellulose acetate-based reverse osmosis membranes) and composite membranes with polyamide as a functional layer (hereinafter referred to as polyamide-based reverse osmosis membranes). Examples of the cellulose acetate-based polymer include ones using organic acid esters of cellulose such as cellulose acetate, cellulose diacetate, cellulose triacetate, cellulose propionate, or cellulose butyrate alone; or a mixture of these; and a mixed ester. Examples of polyamide include linear polymers and cross-linked polymers with aliphatic and/or aromatic diamines as monomers.

Concrete examples of the reverse osmosis membrane include, in addition to ultra low pressure types SUL-G10 and SUL-G20, and low pressure types SU-710, SU-720, SU-720F, SU-710L, SU-720L, SU-720LF, SU-720R, SU-710P, and SU-720P, which are polyamide-based reverse osmosis membrane modules manufactured by Toray Industries, Inc.; high pressure types containing UTC80 as a reverse osmosis membrane SU-810, SU-820, SU-820L, and SU-820FA; cellulose acetate-based reverse osmosis membranes SC-L100R, SC-L200R, SC-1100, SC-1200, SC-2100, SC-2200, SC-3100, SC-3200, SC-8100, and SC-8200, which are manufactured by the same company; NTR-759HR, NTR-729HF, NTR-70SWC, ES10-D, ES20-D, ES20-U, ES15-D, ES15-U, and LF10-D, which are manufactured by Denko Corporation; RO98pHt, RO99, HR98PP, and CE4040C-30D, which are manufactured by Alfa Laval; GE Sepa manufactured by GE, BW30-4040, TW30-4040, XLE-4040, LP-4040, LE-4040, SW30-4040, and SW30HRLE-4040, which are manufactured by Filmtec; TFC-HR and TFC-ULP, which are manufactured by KOCH; ACM-1, ACM-2, and ACM-4, which are manufactured by TRISEP.

As an effect of concentrating a sugar liquid by using a nanofiltration membrane and/or a reverse osmosis membrane, there are advantages of increasing the sugar concentration in the sugar liquid and of enabling fermentation inhibitors to be removed as a permeate. The fermentation inhibitor, when used herein, refers to components other than sugars, the components inhibit fermentation in a fermentation step described later; and specific examples thereof can include aromatic compounds, furan-based compounds, organic acids, and monovalent inorganic salts. Examples of such representative aromatic compounds and furan-based compounds include furfural, hydroxymethylfurfural, vanillin, vanillic acid, syringic acid, coniferyl aldehyde, coumaric acid, and ferulic acid. Examples of organic acids and inorganic salts include acetic acid, formic acid, potassium, and sodium. The sugar concentration of the concentrated sugar liquid can be optionally set at 50 g/L to 400 g/L depending on treatment conditions of the nanofiltration membrane and/or the reverse osmosis membrane and need only to optionally set according to use application of the concentrated sugar liquid or the like. Further, when more removal of the fermentation inhibitor described earlier is desired, what only need to do is to add water to the sugar liquid or the concentrated sugar liquid and concentrate with the nanofiltration membrane and/or the reverse osmosis membrane until an intended sugar concentration is attained; and, under this circumstance, the fermentation inhibitor can be removed as a permeate. It is to be noted that the nanofiltration membrane is preferred because the removal effect is higher when the nanofiltration membrane is used, as compared to when the reverse osmosis membrane is used. Whether to use the nanofiltration membrane or to use the reverse osmosis membrane only need to be determined in the light of the concentration of the fermentation inhibitor contained in the mixed sugar liquid or influence in fermentation described later.

Use Application of Sugar Liquid

Various chemical substances can be produced by growing microorganisms having an ability to produce the chemical substances using the sugar liquid obtained by our methods as a fermentation raw material. To grow a microorganism as a fermentation raw material herein means proliferation and maintained growth of a microorganism using sugar components or amino sources contained in the sugar liquid as nutrients of the microorganism. Concrete examples of the chemical substance can include substances produced in a large scale in the fermentation industry such as alcohols, organic acids, amino acids, or nucleic acids. Such chemical substances are accumulated and produced as chemical substances inside or outside of the organism in the process of metabolism using the sugar component in the sugar liquid as a carbon source. Concrete examples of chemical substances producible by the microorganism include alcohol such as ethanol, 1,3-propanediol, 1,4-butanediol, or glycerol; organic acids such as acetic acid, lactic acid, pyruvic acid, succinic acid, malic acid, itaconic acid, or citric acid; nucleosides such as inosine or guanosine, nucleotides such as inosinic acid or guanylic acid, and amine compounds such as cadaverine. Further, the sugar liquid can be applied to production of enzymes, antibiotics, recombinant proteins, or the like. These microorganisms for use in the production of the chemical substance only need to be microorganisms that can efficiently produce an intended chemical substance; and microorganisms such as *Escherichia coli*, yeast, filamentous fungi, or basidiomycetes can be used.

Apparatus

Apparatuses that carry out the method of producing a sugar liquid will be described based on FIGS. 1 to 4.

FIG. 1 is an apparatus that produces a sugar liquid comprising the hydrothermal treatment apparatus (1) for hydrothermal treatment of the cellulose-containing biomass and solid-liquid separation of the hydrothermally-treated product; the hydrolysis apparatus (14) for hydrolysis of a cellulose-containing solid content discharged from the hydrothermal treatment apparatus by filamentous fungus-derived cellulase; the sugar liquid recovery apparatus (23) for solid-liquid separation of a hydrolysate of the cellulose-containing solid content obtained in the hydrolysis apparatus; and the enzyme recovery apparatus (28) for mixture, thermal retention, and solid-liquid separation of saccharification residues separated by the sugar liquid recovery apparatus and the hydrothermally-treated liquid discharged from the hydrothermal treatment apparatus.

Figure 2:
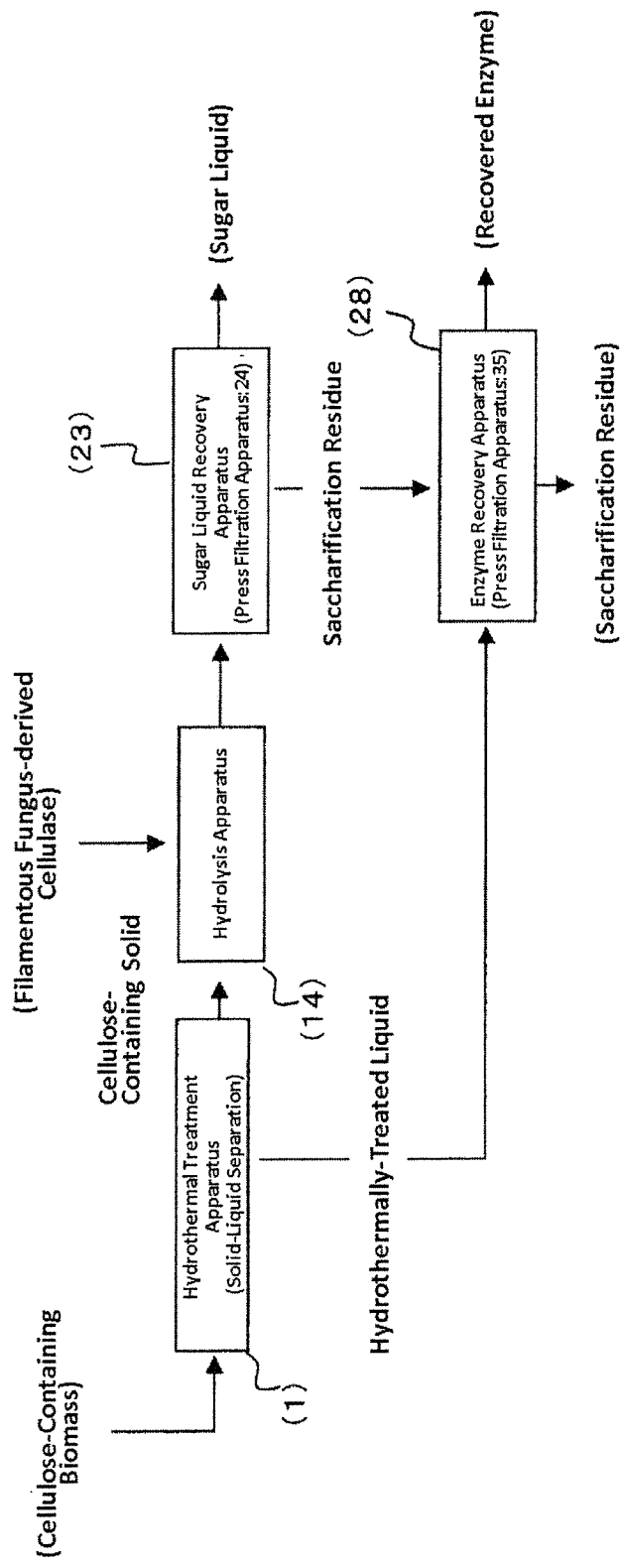
FIG. 2 is a drawing showing one example of an apparatus that carries out the method of producing a sugar liquid (the case of using a press filtration apparatus as a sugar liquid recovery apparatus and an enzyme recovery apparatus).
Figure 3:
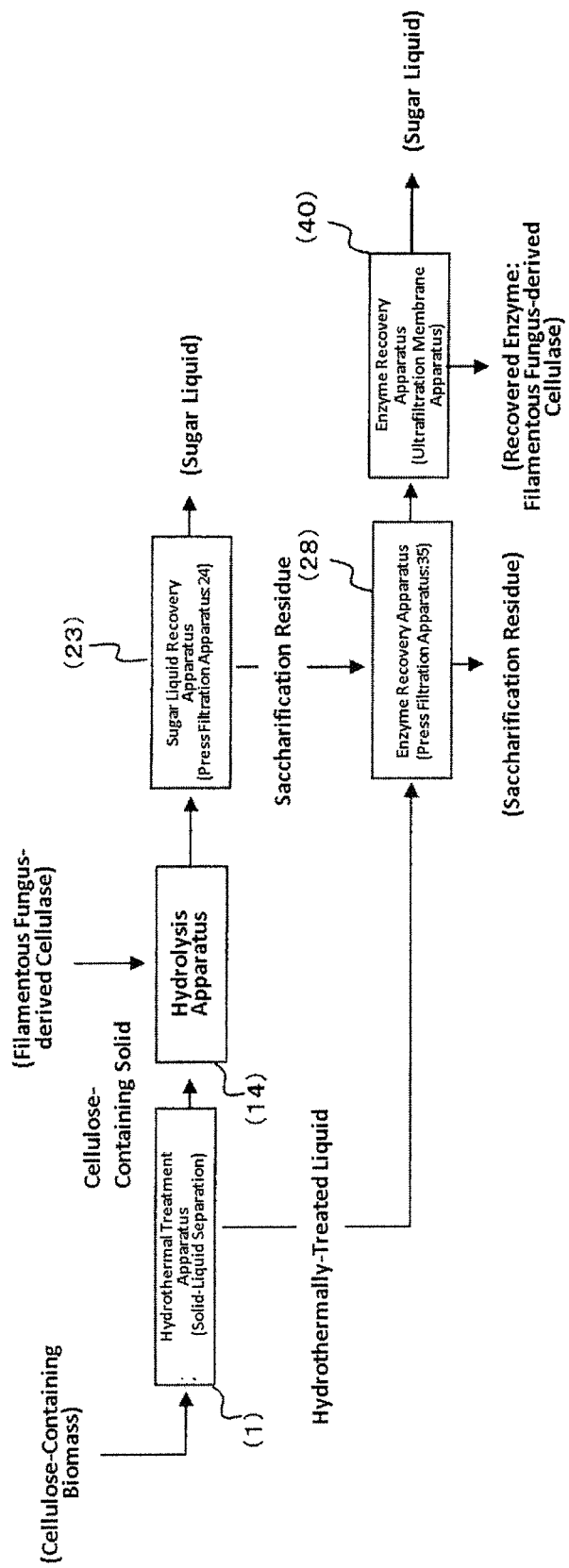
FIG. 3 is a drawing showing one example of an apparatus that carries out the method of producing a sugar liquid (the case of adding an ultrafiltration membrane apparatus as an enzyme recovery apparatus).

FIG. 2 is an example of an apparatus comprising the press filtration apparatus (24, 35) especially in the solid-liquid separation of the sugar liquid recovery apparatus and the enzyme recovery apparatus; and FIG. 3 is an example of an apparatus comprising the ultrafiltration membrane separation apparatus (40) for further separation of filamentous fungus-derived cellulase and a sugar liquid.

Figure 4:
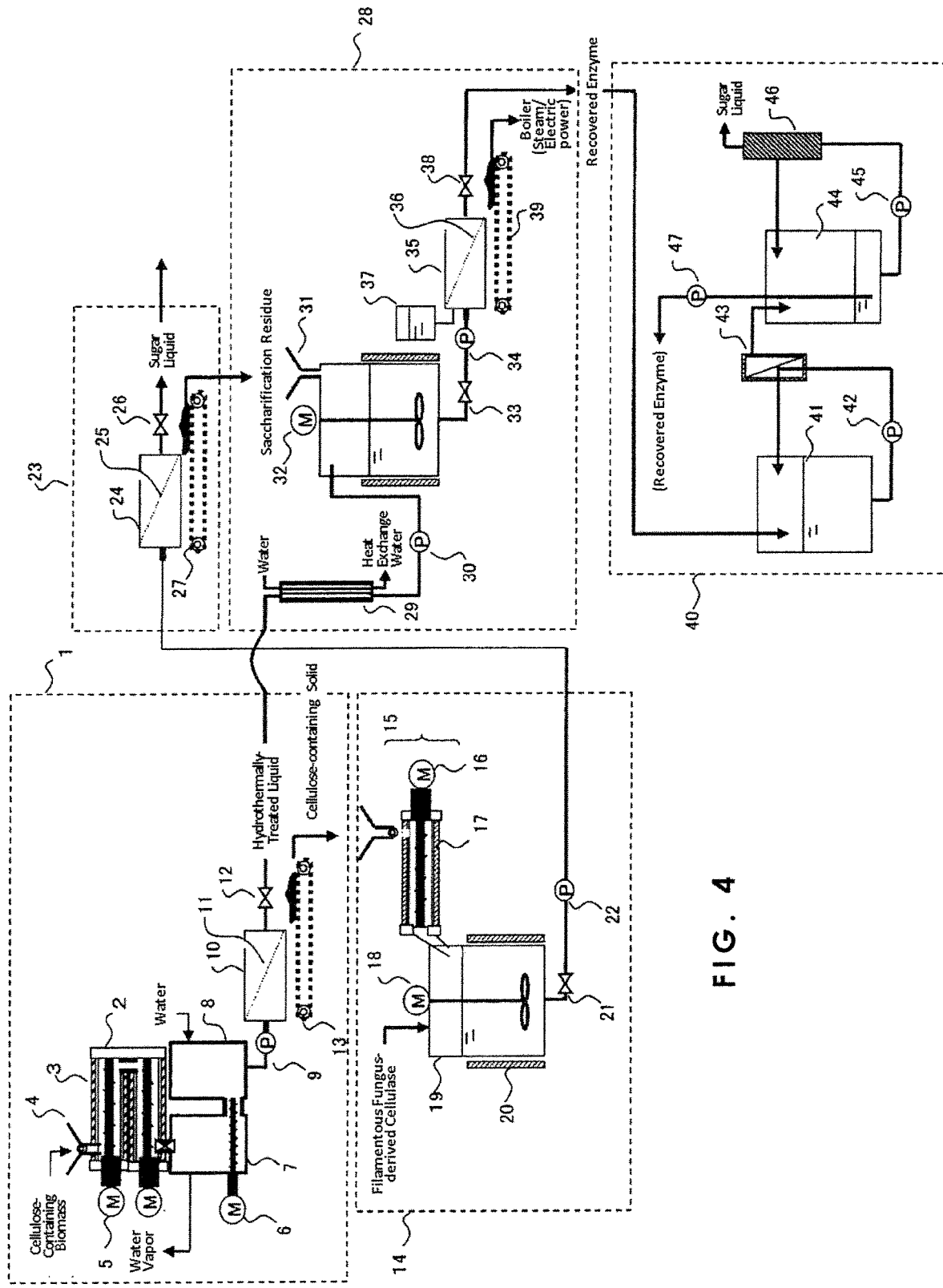
FIG. 4 is a drawing showing details of the production apparatuses for the sugar liquid of FIGS. 1 to 3.

Next, to describe the apparatus for producing a sugar liquid in detail shown in FIGS. 1 to 3, the apparatus configuration will be described by referring to FIG. 4. It is preferred that the hydrothermal treatment apparatus (1) for hydrothermal treatment of cellulose-containing biomass and solid-liquid separation of a hydrothermally-treated product be an apparatus comprising the thermal retention pressurized vessel (2) to carry out a hydrothermal treatment; the heater (3) to heat the above-mentioned thermal retention pressurized vessel (2); the raw material feeder (4) to feed the biomass to the thermal retention pressurized vessel (2); the stirring apparatus (5) that mixes the cellulose-containing biomass in the thermal retention pressurized vessel; the pressure release tank (7) that releases the pressure of the thermal retention pressurized vessel (2); the water dilution tank (8) that dilutes the hydrothermally-treated product with water; the transfer apparatus (6) that transfers the hydrothermally-treated product from the pressure release tank (7) to the water dilution tank (8); the solid-liquid separator (10) that subjects the hydrothermally-treated product to solid-liquid separation; the pump (9) that transfers the hydrothermally-treated product to the solid-liquid separator (10); the separation membrane (11) installed inside the solid-liquid separator (10); and the valve (12) that regulates the discharge of the hydrothermally-treated liquid. The heater (3) can preferably heat the thermal retention pressurized vessel (2) until the cellulose-containing biomass reaches a given temperature (170° C. to 220° C.). The stirring apparatus (5) is preferably one capable of making the cellulose-containing biomass move continuously inside of the thermal retention pressurized vessel (2) and uniformizing the temperature, cellulose-based biomass, and water. Further, by continuously or intermittently feeding fresh cellulose-containing biomass to the thermal retention pressurized vessel (2) via the feeding raw material feeder (4), a continuous hydrothermal treatment of the cellulose-containing biomass become feasible. The solid-liquid separator (10) involves centrifugation, filtration, sedimentation separation, or the like; and a separation method utilizing the separation membrane (11) is preferred because a cellulose-containing solid content with a high solid concentration can be obtained. The material of the separation membrane (11) is as appropriate selected from metal mesh, woven fabric, non-woven fabric, and the like. Because the separated cellulose-containing solid content is a solid, it is preferred to use the belt conveyor (13) to transfer the solid content to the hydrolysis apparatus (14).

With regard to the hydrolysis apparatus (14) for hydrolysis of the cellulose-containing solid content discharged from the hydrothermal treatment apparatus by filamentous fungus-derived cellulase, it is preferred to carry out a primary hydrolysis for the purpose of homogeneously mixing the cellulose-containing solid content and the filamentous fungus-derived cellulase and of decreasing the viscosity thereof by using the kneader (15) that carries out the hydrolysis of the cellulose-containing solid content by the filamentous fungus-derived cellulase. The kneader (15) preferably has the stirring liquid transfer apparatus (16) and the heater (17) to set a temperature for hydrolysis. Further, subsequently to the primary hydrolysis by the kneader (15), a secondary hydrolysis is carried out while stirring and mixing by the stirring apparatus (18) in the stirring tank (19). Like the kneader (15), the stirring tank (19) preferably has the heater (20). The lower part of the stirring tank (19) preferably has, via the valve (21), the pump (22) for transferring a liquid.

The sugar liquid recovery apparatus (23) in which the hydrolysate of the cellulose-containing solid content obtained by the hydrolysis apparatus is subjected to solid-liquid separation may have the solid-liquid separator (24) that separates the sugar liquid from the saccharification residue; and further the solid-liquid separator may have the separation membrane (25) for separation and the valve (26). The saccharification residue is transferred to the enzyme recovery apparatus (28) by using the belt conveyor (27).

The enzyme recovery apparatus (28) for mixture, thermal retention, and solid-liquid separation of the saccharification residue separated by the sugar liquid recovery apparatus and the hydrothermally-treated liquid discharged from the hydrothermal treatment apparatus preferably has the heat exchanger (29) that subjects the hydrothermally-treated liquid to heat exchange; and the thermal retention tank (31), the stirring apparatus (32), and the thermal retention apparatus (30) for mixing the hydrothermally-treated liquid with the saccharification residue and for the thermal retention. The thermal retention tank (31) links, via the valve (33) and the pump (34), to the solid-liquid separator (35), where the saccharification residue and the recovered enzyme are separated. The solid-liquid separator (35) preferably has the separation membrane (36); and the recovered enzyme liquid can be controlled by using the valve (38). The separated saccharification residue is washed by the washing liquid in the washing liquid tank (37) to recover the enzyme component in the saccharification residue. Further, the saccharification residue obtained by the solid-liquid separation is discharged by the belt conveyor (39). The discharged saccharification residue is transferred to a boiler to convert steam and electric power which are preferably used in the production of the sugar liquid. The enzyme recovery apparatus (28) preferably further comprises the ultrafiltration membrane separation apparatus (40) for separating the filamentous fungus-derived cellulase from the sugar liquid. Further, in the ultrafiltration membrane separation apparatus (40), the sugar liquid storage tank (41), the microfiltration membrane pump (42), and the microfiltration membrane module (43) are preferably installed to remove the fine particle component as a pretreatment of ultrafiltration. The filtrate of the microfiltration membrane module (43) is recovered the microfiltration membrane filtrate tank (44) for the moment and further subjected to the ultrafiltration membrane module (46) via the ultrafiltration membrane pump (45), which enables the cellulase and hemicellulase component to be separated and recovered as a retentate. The separated enzyme component can be recovered as an enzyme concentrated liquid in the microfiltration membrane filtrate tank (44). Further, the recovered enzyme concentrated liquid is transferred, as a recovered enzyme, to the cellulose hydrolysis apparatus (14) by using the pump (47). In the meantime, the permeate of the ultrafiltration membrane module (46) can be used as a sugar liquid which serves as a raw material for various types of productions by fermentation.

Figure 6:
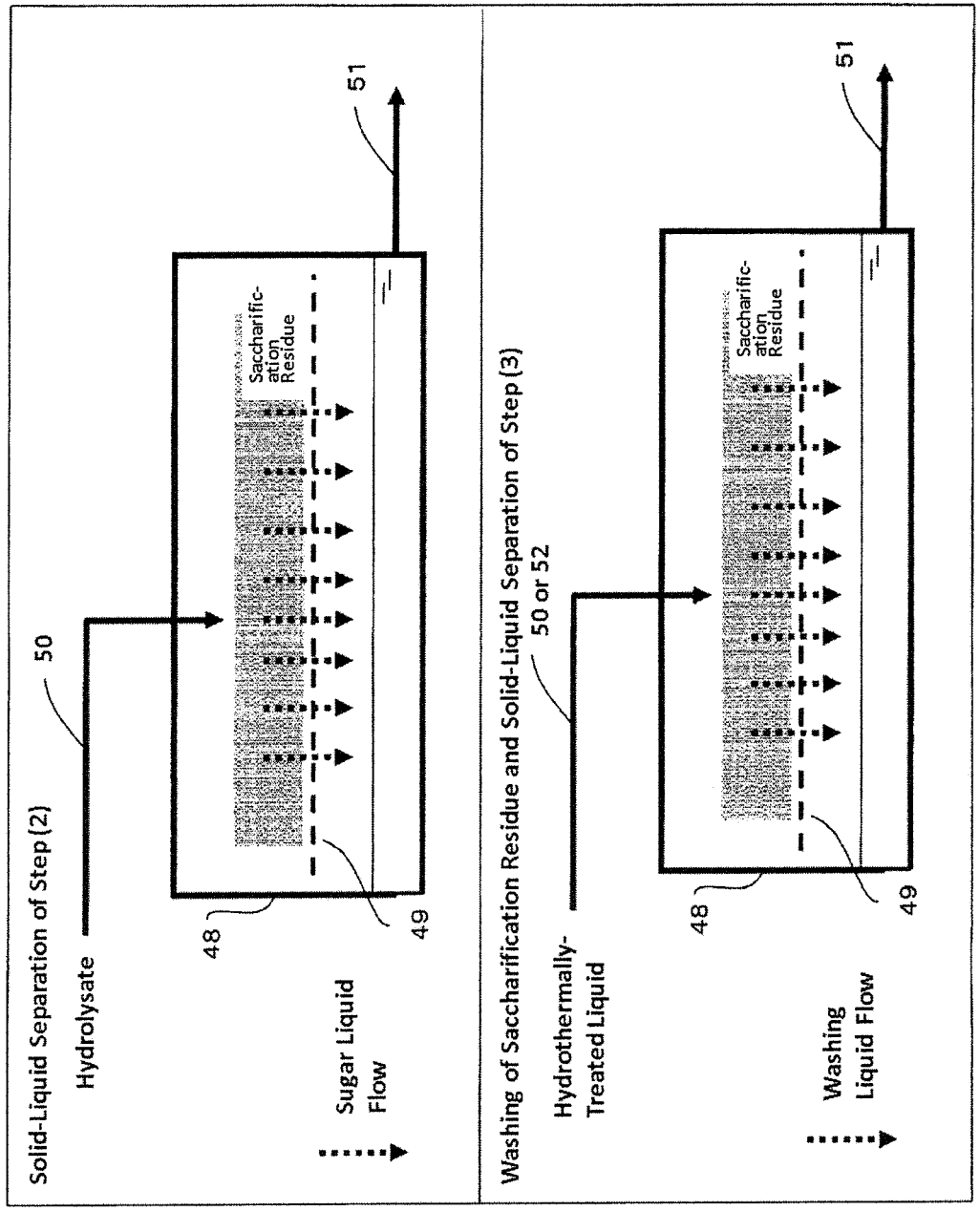
FIG. 6 is a schematic diagram when the solid-liquid separation in the step (2) and the washing of saccharification residue and solid-liquid separation in the step (3) are carried out in the same apparatus (membrane separation apparatus).

Further, FIG. 6 shows a schematic diagram of the case where the solid-liquid separation of the step (2) and the solid-liquid separation of the step (3) are carried out in the same apparatus (the membrane separation apparatus). The hydrolysate obtained in the step (2) is supplied to the membrane separation apparatus 48 (preferably, the press filtration apparatus or the belt filtration apparatus) through the hydrolysate supply line 50. The membrane 49 is installed in the membrane separation apparatus 48; and, by a pressure from the membrane side or a negative pressure from the permeate side, the saccharification residue is separated onto the feed side of the membrane 49 and the sugar liquid is separated into the permeate side. The obtained sugar liquid is recovered by the recovery line 51. Further, as for the saccharification residue separated on the membrane surface, the hydrothermally-treated liquid can be supplied to the saccharification residue through the hydrolysate supply line 50 which is the same as described in the step (2) or the hydrothermal treatment supply line 51 which is independent of the hydrolysate supply line 50. The hydrothermally-treated liquid supplied to the saccharification residue passes through the saccharification residue by a pressure from the membrane side or a negative pressure from the permeate side to be further recovered in the permeate side of the membrane. In that occasion, the saccharification residue can be washed by the hydrothermally-treated liquid. Further, the washing liquid can be recovered from the recovery line 51; and the recovered washing liquid can be further passed through the saccharification residue multiple times through the hydrolysate supply line 50 or the hydrothermal treatment supply line 51.

EXAMPLES

By way of example, our methods will now be concretely described below. This disclosure is, however, not limited thereto.

Reference Example 1

Measurement of the Concentration of Sugars

The concentration of glucose and xylose that were contained in a sugar liquid was quantified in HPLC conditions described below by comparing to a standard sample.
Column: Luna $NH_2$ (manufactured by Phenomenex)
Mobile phase: Milli-Q:acetonitrile=25:75 (flow rate 0.6 mL/min)
Reaction liquid: None
Detection method: RI (differential refractive index)
Temperature: 30° C.

Reference Example 2

Method of Measuring the Recovered Enzyme Activity of Filamentous Fungus-derived Cellulase The recovered enzyme amount of filamentous fungus-derived cellulase that could be recovered in the step (3) was quantified by measuring three kinds of degrading activities (hereinafter referred to as activity value): 1) crystalline cellulose degrading activity, 2) cellobiose degrading activity, and 3) xylan degrading activity.
(1) Crystalline Cellulose Degrading Activity
To an enzyme liquid (prepared in predetermined conditions), Avicel which is crystalline cellulose (Cellulose Microcrystalline manufactured by Merck) 1 g/L and sodium acetate buffer (pH 5.0) were added at 100 mM. The resulting mixture was allowed to react at 50° C. for 24 hours. The reaction liquid was prepared in a 1 mL tube; and the reaction was carried out while rotated and mixed in the above-mentioned condition. After the reaction, the tube was centrifuged; and the glucose concentration of the supernatant component was measured. The glucose concentration was measured in accordance with the method described in Reference Example 2. The concentration of glucose generated (g/L) was used as is as the activity level of the crystalline cellulose degrading activity, which was used for comparison of the amount of enzyme recovered.
(2) Cellobiose Degrading Activity
To an enzyme liquid, cellobiose (manufactured by Wako Pure Chemical Industries, Ltd.) 500 mg/L and sodium acetate buffer (pH 5.0) were added at 100 mM. The resulting mixture was allowed to react 50° C. for 0.5 hours. The reaction liquid was prepared in a 1 mL tube; and the reaction was carried out while rotated and mixed in the above-mentioned condition. After the reaction, the tube was centrifuged; and the glucose concentration of the supernatant component was measured. The glucose concentration was measured in accordance with the method described in Reference Example 2. The concentration of glucose generated (g/L) was used as is as the activity level of the cellobiose degrading activity, which was used for comparison of the amount of enzyme recovered.
(3) Xylan Degrading Activity
To an enzyme liquid, xylan (Birch wood xylan, manufactured by Wako Pure Chemical Industries, Ltd.) 10 g/L and sodium acetate buffer (pH 5.0) were added at 100 mM. The resulting mixture was allowed to react at 50° C. for four hours. The reaction liquid was prepared in a 1 mL tube; and the reaction was carried out while rotated and mixed in the above-mentioned condition. After the reaction, the tube was centrifuged; and the glucose concentration of the supernatant component was measured. The xylose concentration was measured in accordance with the method described in Reference Example 2. The concentration of xylose generated (g/L) was used as is as the activity level of the xylose degrading activity, which was used for comparison of the amount of enzyme recovered.

Reference Example 3

Measurement of the Concentration of Inorganic Ions, Aromatic Compounds, Acetic Acid, Formic Acid, and Lactic Acid The concentration of cations and anions, aromatic compounds, acetic acid, and formic acid in the sugar liquid was quantified under HPLC conditions shown below by comparison with standard samples.
1) Analysis of Cations
Column: Ion Pac AS22 (manufactured by DIONEX)
Mobile phase: 4.5 mM $Na_2CO_3$/1.4 mM $NaHCO_3$ (flow rate 1.0 mL/min)
Reaction solution: none
Detection method: electrical conductivity (with a suppressor being used)
Temperature: 30° C.
2) Analysis of Anions
Column: Ion Pac CS12A (manufactured by DIONEX)
Mobile phase: 20 mM methanesulfonic acid (flow rate 1.0 mL/min)
Reaction solution: none
Detection method: electrical conductivity (with a suppressor being used)
Temperature: 30° C.
3) Analysis of Aromatic Compounds
Column: Synergi HidroRP 4.6 mm×250 mm (manufactured by Phenomenex)
Mobile phase: acetonitrile-0.1% $H_3PO_4$ (flow rate 1.0 mL/min)

Detection method: UV (283 nm)
Temperature: 40° C.
4) Analysis of Acetic Acid, Formic Acid, and Lactic Acid
Column: Shim-Pack SPR-H (manufactured by Shimadzu Corporation) in series
Mobile phase: 5 mM p-toluenesulfonic acid (flow rate 0.8 mL/min)
Reaction solution: 5 mM p-toluenesulfonic acid, 20 mM bis tris, 0.1 mM EDTA.2Na (flow rate 0.8 mL/min)
Detection method: electrical conductivity
Temperature: 45° C.

Reference Example 4

Method of Analyzing Structural Sugars in the Hydrothermally-treated Product of Cellulose-containing Biomass By reference to the LAP method ("Determination of Structural Carbohydrates and Lignin in Biomass, Laboratory Analytical Procedure (LAP)"), the composition was analyzed by the following method.

An appropriate amount of a sample was aliquoted and the water content thereof was measured by the method in the above Reference Example 2. Subsequently, after calculating the water content of Reference Example 2, the obtained dried sample was subjected to ignition at a temperature of 600° C. to determine the ash content thereof.

Further, the sample was transferred to a stainless steel vat and air-dried in the laboratory atmosphere to be roughly in the equilibrium state; and the resultant was ground by a Wiley mill and passed through a sieve to adjust its particle size to about 200 to 500 μm. The sample after this adjustment was dried in vacuum at a temperature of 60° C.; and the content of each component on an absolute dry base was determined by correcting absolute dry mass. To a beaker, 0.3 g of this sample for analysis was measured by a scale balance; and 3 mL of sulfuric acid with a concentration of 72% was added thereto and left to stand, while occasionally stirred, at a temperature of 30° C. for one hour. This reaction solution was completely transferred to a pressure bottle with 84 mL of purified water and then autoclaved for thermolysis at a temperature of 120° C. for one hour. After the thermolysis, a degraded liquid and residue were filtered out and added to a filtrate and a washing liquid of residues to make a constant volume of 100 mL. The resultant was used as a test liquid. Further, a spiked recovery test using monosaccharides was simultaneously carried out at the time of thermolysis for the purpose of correcting excessive breakdown of sugars. With regard to the monosaccharide (xylose, arabinose, mannose, glucose, and galactose) in the test liquid, quantification was carried out by a high-speed liquid chromatography method (GL-7400 manufactured by GL Sciences Inc., fluorescence detection). From the monosaccharide concentration of the obtained degraded liquid and the amount of the sample broken down, the amount of structural in the sample was determined.

Example 1

Setup of Hydrothermal Treatment Conditions (Step (1))

Rice straw was ground at a rotational speed of 420 revolution/min by using a rotary cutter mill.RCM-400 (8 mm mesh) manufactured by Nara Machinery Co., Ltd. Thereafter, hydrothermal treatment was carried out. A blasting apparatus (reactor 2 L size) manufactured by Nihon Dennetsu Co., Ltd. was used. As for a steam generator, a 40 kW electric boiler was used. A treatment temperature is unambiguously determined once the treatment pressure is set and therefore, as for the reaction condition, various types of conditions were tested by changing the treatment pressure and treatment time as shown in Table 1. In this condition, 200 g of the ground rice straw was fed per run; a reaction was carried out under the condition of Table 1. The solid content containing water that was obtained by a blasting treatment was added with 2 L of water, stirred, and separated into a hydrothermally-treated liquid and a cellulose-containing solid content using a centrifuge for laboratory "HimacCF7D2" manufactured by Hitachi Koki Co., Ltd. at 5000 rpm. The analysis of the structural sugars in the separated cellulose-containing solid content was carried out. Thereafter, the water content was measured for each of the blasting treatment product. Water and 1 N aqueous sodium hydroxide solution (manufactured by Wako Pure Chemical Industries, Ltd.) was added to adjust the pH in a range of 4.6 to 5.0; and water was further added to adjust a slurry liquid such that the solid concentration was eventually 5%. Further, filamentous fungus-derived cellulase (cellulase derived from *Trichoderma*) "Accellerase DUET" (enzyme concentration: 40 g/L) manufactured by Genencor was added to the slurry liquid such that the enzyme weight is one hundredth of the dry weight of the blasting treated product; and the saccharification rate of the glucose component and the xylose component was measured. The results are shown in Table 1.

TABLE 1

Hydrothermal treatment condition and saccharification rate

| Test No. | Treatment time | Pressure | Temperature (° C.) | Cellulose saccharification rate (%) | Xylan saccharification rate (%) |
|---|---|---|---|---|---|
| 1 | 5 minutes | 3.5 MPa | 243 | 82 | — |
| 2 | 2.5 minutes | 3.5 MPa | 243 | 82 | — |
| 3 | 5 minutes | 3 MPa | 235 | 82 | — |
| 4 | 2.5 minutes | 3 MPa | 235 | 83 | 100 |
| 5 | 5 minutes | 2.5 MPa | 225 | 82 | 100 |
| 6 | 2.5 minutes | 2.5 MPa | 225 | 80 | 99 |
| 7 | 5 minutes | 2.0 MPa | 215 | 75 | 85 |
| 8 | 2.5 minutes | 2.0 MPa | 215 | 56 | 75 |
| 9 | 5 minutes | 1.5 MPa | 200 | 57 | 70 |
| 10 | 2.5 minutes | 1.5 MPa | 200 | 40 | 60 |
| 11 | 5 minutes | 1.0 MPa | 183 | 35 | 55 |
| 12 | 5 minutes | 0.5 MPa | 157 | 15 | 15 |

From the result of Table 1, when rice straw was used as the cellulose-containing biomass, that it is preferred to carry out a temperature of 180 to 240° C.

Example 2

Preparation of the Hydrothermally-treated Liquid and the Cellulose-containing Solid Content (Step (1))

The hydrothermally-treated product obtained in the condition of the test number 7 described in Example 1 (the condition at 215° C. for 5 minutes) was centrifuged at 3000 G for 10 minutes to separate and recover a hydrothermally-treated liquid; and the obtained solid was further added with water and centrifuged to remove a supernatant. This series of operation was carried out twice. The obtained solids were used in the following Examples and Comparative Examples as a cellulose-containing solid content.

Comparative Example 1

Hydrolysis in Mixing a Cellulose-containing Solid Content with a Hydrothermally-treated Liquid To 1 g of the cellulose-containing solid content of Example 2, "Accellerase DUET" which was used in Example 1 was added to have a final concentration of 1 g/L, 0.8 g/L, 0.5 g/L, and 0.35 g/L and hydrolysis was carried out at 50° C. for 24 hours. Further, preparation was done such that the solid concentration of the cellulose-containing solid content came to be 10 wt % by adding the hydrothermally-treated liquid obtained in Example 2. In addition, the pH at the time of the hydrolysis was adjusted with dilute sulfuric acid and dilute sodium hydroxide to be pH4.6 to 5.4. The obtained hydrolysate was centrifuged to separate 8 g of sugar liquid and 2 g of saccharification residue. The result obtained by measuring the glucose concentration of the sugar liquid was shown in Table 2.

TABLE 2

Hydrolysis in the case of mixing cellulose-containing solid content and hydrothermally treated liquid

| Concentration of enzyme added (g/L) | Reaction time (h) | Glucose concentration (g/L) |
|---|---|---|
| 1 | 4 h | 9 |
|   | 24 h | 25 |
| 0.8 | 4 h | 7 |
|   | 24 h | 22 |
| 0.5 | 4 h | 7 |
|   | 24 h | 21 |
| 0.35 | 4 h | 5 |
|   | 24 h | 18 |

Example 3

Hydrolysis of the Cellulose-containing Solid Content (Step (2))

To 1 g of the cellulose-containing solid content of Example 2, "Accellerase DUET" used in Example 1 was added such that the final concentration thereof came to be 1 g/L, 0.8 g/L, 0.5 g/L, and 0.35 g/L; and hydrolysis was carried out at 50° C. for 24 hours. Further, preparation was done such that the solid concentration of the cellulose-containing solid content came to be 10 wt % by adding RO water. Further, the pH at the time of hydrolysis was adjusted with dilute sulfuric acid and dilute sodium hydroxide to be pH4.6 to 5.4. The obtained hydrolysate was centrifuged and separated into the sugar liquid 8 g and the saccharification residue 2 g. The glucose concentration of the sugar liquid was measured. The result is shown in Table 3.

TABLE 3

Hydrolysis of Cellulose-containing solid content

| Concentration of enzyme added (g/L) | Reaction time (h) | Glucose concentration (g/L) |
|---|---|---|
| 1 | 4 h | 12 |
|   | 24 h | 27 |
| 0.8 | 4 h | 8 |
|   | 24 h | 27 |
| 0.5 | 4 h | 7 |
|   | 24 h | 23 |
| 0.35 | 4 h | 6 |
|   | 24 h | 20 |

Compared to the result of hydrolysis in the case of mixing the cellulose-containing solid content and the hydrothermally-treated liquid in Comparative Example 1 (Table 2), we found that the amount of glucose generated with an identical amount of saccharification enzyme was higher in Example 3 where the cellulose-containing solid content alone was employed. That is, it is shown that the component that inhibits the hydrolysis of the cellulose-containing solid content is included in the hydrothermally-treated liquid; and the separation increases the amount of glucose generated and the amount of sugars generated.

Comparative Example 2

Enzymatic Saccharification of the Hydrothermally-treated Liquid

To the hydrothermally-treated liquid obtained in Example 2, "Accellerase DUET" used in Example 1 was added such that the final concentration thereof came to be 0.04 g/L to 0.8 g/L; and hydrolysis was carried out at 50° C. for 24 hours. After the reaction, the hydrothermally-treated liquid was centrifuged; and the concentration of glucose and xylose in the supernatant component was measured. The obtained analysis result is shown in Table 4.

TABLE 4

Hydrolysis of hydrothermally treated liquid

| Concentration of enzyme added (g/L) | Sugar component | Sugar concentration (g/L) |
|---|---|---|
| 0.8 | Glucose | 7.69 |
|   | Xylose | 18.48 |
| 0.4 | Glucose | 6.79 |
|   | Xylose | 16.45 |
| 0.32 | Glucose | 6.80 |
|   | Xylose | 15.82 |
| 0.24 | Glucose | 6.79 |
|   | Xylose | 15.67 |
| 0.2 | Glucose | 6.51 |
|   | Xylose | 14.84 |
| 0.16 | Glucose | 6.54 |
|   | Xylose | 14.26 |
| 0.08 | Glucose | 5.86 |
|   | Xylose | 11.15 |
| 0.04 | Glucose | 5.77 |
|   | Xylose | 9.13 |
| 0 | Glucose | 2.97 |
|   | Xylose | 2.27 |

As a result, we found that, as the enzyme concentration increased, the amount of glucose generated and the amount of xylose generated increased.

Further, we found that, even if the enzyme concentration was 0.16 g/L or more the amount of sugar generated did not increase greatly in the reaction at 50° C. for 24 hours. We thus found that, to perform sufficient hydrolysis of the hydrothermally-treated liquid in the reaction at 50° C. for 24 hours, 0.16 g/L enzyme was required to be added.

Example 4

Washing of Saccharification Residues with the Hydrothermally-treated Liquid (Step (3))

To 2 g of saccharification residue (including water) obtained when the concentration of "Accellerase DUET" added was 0.8 g/L in Example 3, the hydrothermally-treated liquid was added at a weight ratio of 1:4 or 1:8 and kept the temperature at 50° C. for 0 hours, 6 hours, 24 hours, 48 hours, or 72 hours to wash the saccharification residue. After the washing, the washing liquid at each reaction time was centrifuged (8000 G, 20 minutes) to recover the supernatant (the case of 1:4: 8 g, the case of 1:8: 16 g); and the concentration of glucose and xylose contained in the washing liquid was measured by the technique in Reference Example 1. This result is shown in Tables 5 and 6.

Comparative Example 3

Washing of Saccharification Residue by RO Water

To a weight of 2 g of saccharification residue (including water) of Example 4, RO water was added at a ratio of 1:4 or 1:8 and the temperature thereof was kept at 50° C. for 0 hours, 6 hours, 24 hours, 48 hours, and 72 hours. The supernatant was recovered by centrifugation (8000 G, 20 minutes) (the case of 1:4: 8 g, the case of 1:8: 16 g). The concentration of glucose and xylose in each supernatant was measured by the technique in Reference Example 1. The result is shown in Table 5 and Table 6.

TABLE 5

Washing of saccharification residue by hydrothermally treated liquid: Amount of glucose generated

| Saccharification residue:hydrothermally treated liquid | | 0 h. | 6 h. | 24 h. | 48 h. | 72 h. |
|---|---|---|---|---|---|---|
| 1:4 | Example 4 | 7.3 | 16 | 17 | 19 | 19 |
|  | Comparative Example 3 | 5.1 | 13 | 14 | 15 | 15 |
| 1:10 | Example 4 | 4.8 | 9.8 | 9.5 | 11 | 12 |
|  | Comparative Example 3 | 2.2 | 5.4 | 5.8 | 6.8 | 6.7 |

TABLE 6

Washing of saccharification residue by hydrothermally treated liquid: Amount of xylose generated

| Saccharification residue:hydrothermally treated liquid | | 0 h. | 6 h. | 24 h. | 48 h. | 72 h. |
|---|---|---|---|---|---|---|
| 1:4 | Example 4 | 2.6 | 16 | 15 | 17 | 17 |
|  | Comparative Example 3 | 0.4 | 0.6 | 0.9 | 0.8 | 0.8 |
| 1:10 | Example 4 | 2.5 | 16 | 15 | 18 | 18 |
|  | Comparative Example 3 | 0.3 | 0.3 | 0.4 | 0.3 | 0.4 |

As shown in Tables 5 and 6, we found that when the hydrothermally-treated liquid was added to the saccharification residue and kept warm, the amount of glucose and xylose generated increased. The ratio of the saccharification residue to the hydrothermally-treated liquid was changed (saccharification residue:hydrothermally-treated liquid was 1:4 and 1:8) and the same study was conducted; and we found that the amount of glucose and xylose generated increased in both studies. In addition, we found that just adding RO water to the saccharification residue and keeping the resultant warm solely increased the amount of sugars generated, in particular, the amount of glucose generated.

In the meantime, we found that the amount of xylose generated in Example 4 increased, as compared with that in Comparative Example 3 (Table 6). This was thought to be because xylan or xylooligosaccharide in the hydrothermally-treated liquid was hydrolyzed by the action of enzyme components adsorbed in the saccharification residue. This is consistent with a tendency that the amount of xylose generated, in particular, markedly increases by adding the filamentous fungus-derived cellulase to the hydrothermally-treated liquid of Comparative Example 2 described earlier.

Example 5

Recovery of Enzymes from the Saccharification Residue Washing Liquid by Hydrothermally-treated Liquid (Step (4))

To 2 g of saccharification residue (including water) obtained when the concentration of "Accellerase DUET" added was 0.8 g/L in Example 3, the hydrothermally-treated liquid was added at a weight ratio of 1:4 and kept the temperature at 50° C. for 24 hours to wash the saccharification residue. After the washing, the washing liquid at each reaction time was centrifuged (8000 G, 20 minutes) to recover the supernatant, thereby obtaining 8 g of the washing liquid. The above-mentioned washing liquid 8 g was further filtered using Millex HV filter unit filtration (Millipore, 33 mm, made of PVDF, fine pore size 0.45 μm). The obtained filtrate was filtered with an ultrafiltration membrane with a molecular weight cut off of 10000 (VIVASPIN 20 manufactured by Sartorius stedim biotech, material: PES); and a membrane fraction was centrifuged at 4500 G until the volume thereof reached 1 mL. Distilled water 10 mL was added to the membrane fraction and again centrifuged at 4500 G until the volume of the membrane fraction reached 0.5 mL. Thereafter, the enzyme was recovered from the membrane fraction. Each activity of the recovered enzyme was measured in accordance with Reference Example 2. Further, for the sake of comparison, each enzyme activity of "Accellerase DUET" (0.8 g/L) by itself was measured in accordance with Reference Example 2; and the activity at that time was used as 100(%) to determine a relative value. The activity of cellulase and hemicellulase is summarized in Table 7 as expressed by the terms of the relative value.

Comparative Example 4

Recovery of Filamentous Fungus-derived Cellulase in the Case of the Filtering Sugar Liquid Obtained by Hydrolysis of the Cellulose-Containing Solid Content Through the Ultrafiltration Membrane The sugar liquid (8 g) obtained when the concentration of "Accellerase DUET" added was 0.8 g/L in Example 3 was further filtered using a Millex HV filter unit (Millipore, 33 mm, made of PVDF, fine pore size 0.45 μm). The obtained filtrate was filtered using an ultrafiltration membrane with a molecular weight cut off of 10000 (VIVASPIN 20 manufactured by Sartorius stedim biotech, material: PES); and a membrane fraction was centrifuged at 4500 G until the volume thereof reached 0.5 mL. Distilled water 10 mL was added to the membrane fraction and again centrifuged at 4500 G until the volume of the membrane fraction reached 0.5 mL. Thereafter, the enzyme was recovered from the membrane fraction. Each activity of the recovered enzyme was measured in accordance with Reference Example 4 (Table 7).

Comparative Example 5

Recovery of Enzymes from the Saccharification Residue Washing Liquid by RO Water To 2 g of saccharification residue (including water) obtained when the concentration of "Accellerase DUET" added was 0.8 g/L in Example 3, RO water was added at 1:4 and the resultant was hydrolyzed at 50° C. for 24 hours and further filtered using a Millex HV filter unit (Millipore, 33 mm, made of PVDF, fine pore size 0.45 μm). The obtained filtrate was filtered using an ultrafiltration membrane with a molecular weight cut off of 10000 (VIVASPIN 20 manufactured by Sartorius stedim biotech, material: PES); and a membrane fraction was centrifuged at 4500 G until the volume thereof reached 1 mL. Distilled water 10 mL was added to the membrane fraction and again centrifuged at 4500 G until the volume of the membrane fraction reached 0.5 mL. Thereafter, the enzyme was recovered from the membrane fraction. Each activity of the recovered enzyme was measured in accordance with Reference Example 4 (Table 7).

TABLE 7

Recovered enzyme and each enzyme activity

|  |  | Avicel degrading activity (%) | Cellobiose degrading activity (%) | Xylan degrading activity (%) |
|---|---|---|---|---|
| Cellulase dilution liquid |  | 100 (standard) | 100 (standard) | 100 (standard) |
| Recovered enzyme | Comparative Example 4 | 1 | 3 | 0 |
|  | Example 5 | 34 | 63 | 74 |
|  | Comparative Example 5 | 1 | 5 | 0 |

When the activity of enzyme recovered from the sugar liquid derived from the cellulose-containing solid content was compared with the activity of enzyme recovered from the saccharification residue washing liquid by the hydrothermally-treated liquid, it was found that each of the activities (Avicel degrading activity, cellobiose degrading activity, and xylan degrading activity) of the enzyme recovered from the saccharification residue washing liquid by the hydrothermally-treated liquid was higher. That is, it was thought that the enzyme recovery was promoted by the component contained in the hydrothermally-treated liquid.

Example 6

Analysis of Components of the Hydrothermally-treated Liquid

Measurement of the concentration of inorganic ions contained in the hydrothermally-treated liquid was carried out by the procedure of Reference Example 3. As a result, as shown in Table 8, we found that the hydrothermally-treated liquid contained 1 g/L or more of inorganic ions and, in particular, a large amount of potassium component.

TABLE 8

Analysis of hydrothermally treated liquid:inorganic ion

|  | $Na^+$ | $NH_4^+$ | $K^+$ | $PO_4^{3-}$ | $SO_4^{2-}$ | $Cl^-$ | Total |
|---|---|---|---|---|---|---|---|
| Hydrothermally treated liquid | 318 | 54 | 4839 | 663 | 144 | 1131 | 7149 |

Next, as for the analysis of aromatic components and organic acids, the measurement was carried out by the procedure of Reference Example 3. As a result, as shown in Table 9, we found that, of the aromatic components, the amount of furfural components was contained in 1 g/L or more. In addition, we found that, of the organic acids, acetic acid components were contained in 1 g/L or more. That is, the result of the analysis of the component of the hydrothermally-treated liquid showed that there was a relationship between improved enzyme recovery in the addition of the hydrothermally-treated liquid and the concentration of the inorganic ion, furfural, and acetic acid contained at an effective level in the hydrothermally-treated liquid.

TABLE 9

Analysis of Hydrothermally treated liquid: aromatic compound•organic ion

|  | Furfural | HMF | Vanillin | Guaiacol | Acetic acid | Formic acid |
|---|---|---|---|---|---|---|
| Hydrothermally treated liquid | 3140 | 564 | 21 | 663 | 4120 | 890 |

Example 7

Separation Analysis of Recovered Enzyme by SDS-PAGE

Figure 5:
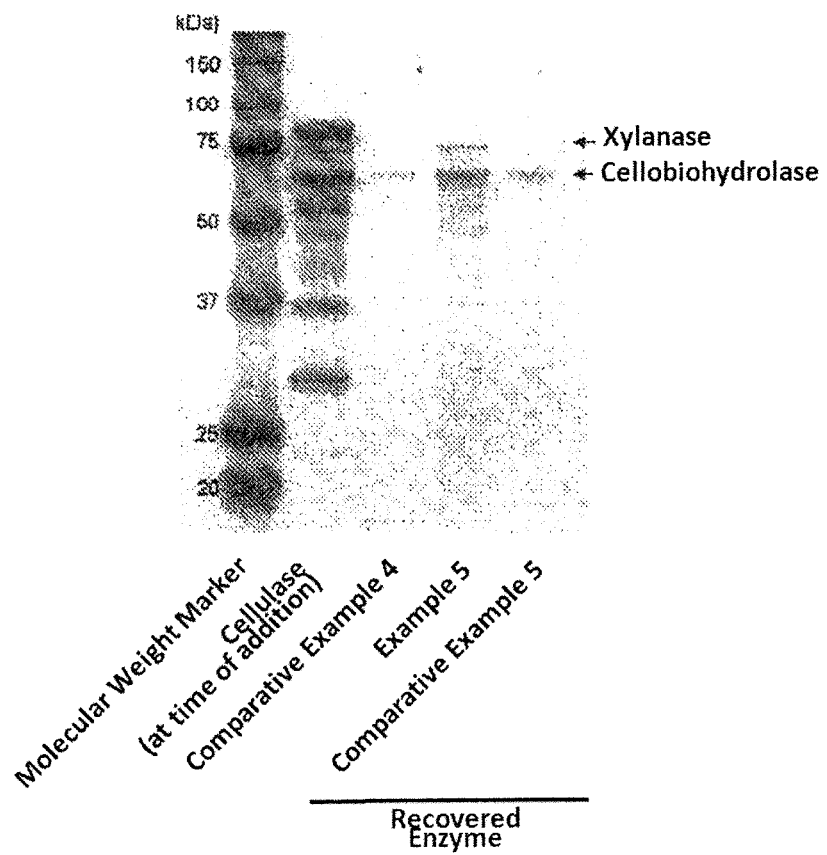
FIG. 5 is a photograph of a gel stained after carrying out SDS-PAGE of a recovered enzyme.

For each of the recovered enzyme liquids of Comparative Example 4, Comparative Example 5, and Example 5, analysis by SDS-PAGE was carried out. To each recovered enzyme liquid, a sample preparation liquid buffer (Ez Apply, ATTO) was added to perform SDS-PAGE (e-PAGEL, 15% gel concentration, ATTO). Staining was carried out using Coomassie Brilliant Blue (BioSafecoomassie Stain, Bio-RAD). Note that a molecular weight marker (Precision Plus Protein Standard, Kaleidoscope, BioRAD) was used to measure the molecular weight. The result is shown in FIG. 5. It was able to be confirmed that the recovered enzyme component of Example 5 increased as compared those of Comparative Examples 4 and 5. In addition, by comparison with the molecular weight marker, we were able to confirm that components exhibiting improved recovery in Example 5 were a cellobiohydrolase component and a xylanase component (FIG. 5).

Example 8

Ethanol Production by Fermentation with the Sugar Liquid as a Fermentation Raw Material Using the sugar liquid obtained in Example 4 as a fermentation raw material, an ethanol fermentation test by yeast (*Saccharomycecs cerevisiae* OC-2: wine yeast) was carried out. The aforementioned yeast was precultured in YPD medium (2% glucose, 1% yeast extract (Bacto Yeast Extract/BD), 2% polypeptone (manufactured by Nihon Pharmaceutical Co., Ltd.)) at 25° C. for one day. Subsequently, the obtained culture liquid was added the first sugar liquid to be 1%. After added, the microorganism was incubated at 25° C. for two days. The cumulative concentration of ethanol contained in the culture liquid obtained by this operation was measured by a gas chromatography method (using Shimadzu GC-2010 capillary GC TC-1 (GL science) 15 meter L.*0.53 mm I.D., df 1.5 μm with detection and calculation by a flame ionization detector for evaluation). As a result, it was able to be confirmed that the culture liquid contained 8 g/L ethanol. That is, it was able to be confirmed that ethanol could be produced as the sugar liquid fermentation raw material.

Example 9

Lactic Acid Production by Fermentation with the Sugar Liquid as a Fermentation Raw Material Using the sugar liquid obtained in Example 4 as a fermentation raw material, *Lactococcus lactis* JCM7638 strain which is a *lactobacillus* was subjected to static culture at a temperature of 37° C. for 24 hours. The concentration of L-lactic acid contained in the culture liquid was analyzed in the condition of Reference Example 3. As a result, we confirmed that L-lactic acid accumulated in 11 g/L and we confirmed that lactic acid production is feasible by the sugar liquid.

Example 10

Washing of the Saccharification Residue by the Hydrothermally-treated Liquid (Step (3)): Effect of the Temperature of the Hydrothermally-treated Liquid To 2 g of saccharification residue (including water) obtained when the concentration of "Accellerase DUET" added was 0.8 g/L in Example 3, the hydrothermally-treated liquid was added at a weight ratio of 1:4 and kept the temperature at each of 4° C., 25° C., 40° C., 60° C., 70° C., and 80° C. to wash the saccharification residue. After washing, the washing liquid at each reaction time was centrifuged (8000 G, 20 minutes) to recover the supernatant, thereby obtaining 8 g of the washing liquid. The concentration of glucose and xylose contained in each washing liquid was measured by the technique of Reference Example 1. This result is shown in Tables 10 and 11.

TABLE 10

Effects of temperature of hydrothermally treated liquid on amount of sugars generated: amount of glucose generated

| Temperature | 0 h. | 6 h. | 24 h. | 48 h. | 72 h. |
| --- | --- | --- | --- | --- | --- |
| 4° C. | 7.3 | 8.2 | 8.8 | 8.8 | 8.8 |
| 25° C. | 7.3 | 8 | 9 | 11 | 11 |
| 40° C. | 7.3 | 15 | 17 | 18 | 19 |
| 50° C. (Example 4) | 7.3 | 16 | 17 | 19 | 19 |
| 60° C. | 7.3 | 12 | 14 | 14 | 14 |
| 70° C. | 7.3 | 8.5 | 9.4 | 9.4 | 9.4 |
| 80° C. | 7.3 | 7.3 | 7.3 | 7.3 | 7.5 |

TABLE 11

Effects of temperature of hydrothermally treated liquid on amount of sugars generated: amount of xylose generated

| Temperature | 0 h. | 6 h. | 24 h. | 48 h. | 72 h. |
| --- | --- | --- | --- | --- | --- |
| 4° C. | 2.6 | 5 | 6 | 8 | 8 |
| 25° C. | 2.6 | 7 | 8 | 10 | 12 |
| 40° C. | 2.6 | 14 | 15 | 16 | 17 |
| 50° C. (Example 4) | 2.6 | 16 | 15 | 17 | 17 |
| 60° C. | 2.6 | 9.6 | 10.7 | 10.7 | 10.7 |
| 70° C. | 2.6 | 3.6 | 3.7 | 3.9 | 4.0 |
| 80° C. | 2.6 | 2.6 | 2.6 | 2.6 | 2.6 |

As for the temperature of the hydrothermally-treated liquid at the time of the washing, it was able to be confirmed that 40 to 60° C. is preferred because oligo-hydrolysis in the hydrothermally-treated liquid progressed most and both glucose and xylose in the washing liquid increased.

Example 11

Recovery of Enzymes from the Saccharification Residue Washing Liquid by the Hydrothermally-treated Liquid (Example 10) (Step (4))

Each washing liquid 8 g obtained in Example 10 was filtered by an ultrafiltration membrane in the same procedure as described in Example 5 to recover the enzyme in the washing liquid. Each activity of the recovered enzyme was measured in accordance with Reference Example 2. Further, for the sake of comparison, each enzyme activity of "Accellerase DUET" (0.8 g/L) by itself was measured in accordance with Reference Example 2; and the activity at that time was used as 100(%) to determine a relative value. The activity of cellulase and hemicellulase is summarized in Table 12 as expressed by the terms of the relative value.

TABLE 12

Recovered enzyme and each enzyme activity

| | | Avicel degrading activity (%) | Cellobiose degrading activity (%) | Xylan degrading activity (%) |
| --- | --- | --- | --- | --- |
| Cellulase dilution liquid | | 100 (standard) | 100 (standard) | 100 (standard) |
| Recovered enzyme | 4° C. | 8 | 26 | 34 |
| | 25° C. | 10 | 34 | 49 |
| | 40° C. | 28 | 54 | 70 |
| | 50° C. (Example 5) | 34 | 63 | 74 |
| | 60° C. | 26 | 68 | 65 |
| | 70° C. | 7 | 24 | 1 |
| | 80° C. | 1 | 1 | 1 |

As for the temperature of the hydrothermally-treated liquid at the time of the washing, we confirmed that 40 to 60° C. is preferred because the enzyme activities (Avicel degrading activity, cellobiose degrading activity, and xylan degrading activity) in the washing liquid improved most.

Example 12

Washing of Saccharification Residues by the Hydrothermally-treated Liquid Using the Press Filtration Apparatus (Step (3)), and Recovery of Enzymes from the Washing Liquid (Step (4))

To 100 g of cellulose-containing solid of Example 2, "Accellerase DUET" was added such that the final concentration thereof became 0.8 g/L; and hydrolysis was carried out at 50° C. for 24 hours. On this occasion, the solid concentration in the cellulose-containing solid content was adjusted to 10 wt % by adding RO water (10L in total). The hydrolysate 10 L thus obtained was subjected to press filtration using a small-sized filter press apparatus (filter press MO-4 manufactured by Yabuta Industries Co., Ltd.). As for a filter cloth, a woven fabric made of polyester (T2731C manufactured by Yabuta Industries Co., Ltd.) was used. A slurry liquid 10 L was placed in a small tank. While the slurry liquid was aerated with compressed air from the bottom, a liquid input port was opened and the slurry liquid was gradually fed into a filtration chamber by an air pump (66053-3EB manufactured by Taiyo International Corporation). After the slurry was fed, a filter press filtrate was recovered as a sugar liquid ((step (3))). The hydrothermally-treated liquid was subjected to a compression step by inflating an attached diaphragm. The compression pressure was gradually elevated to 0.5 MPa and left to stand for about 30 minutes to further recover a filtrate as a sugar liquid. The amount of the sugar liquid that was able to be recovered as the filtrate was 7 L. Subsequently, for the saccharification residue separated in the filtration chamber, the temperature was in advance kept at 50° C. and a hydrothermally-treated liquid 5 L was passed and circulated. The hydrothermally-treated liquid was placed in the small tank; the liquid input port was opened; and the hydrothermally-treated liquid was passed through the saccharification residue separated in the filtration chamber by the air pump. After passing, a filtrate was gradually obtained, again kept the temperature thereof at 50° C., and then put back to the small tank; this circular operation was repeated. This operation was carried out at regular intervals for two hours, and the compression pressure was again gradually elevated to 0.5 MPa and left to stand for about 30 minutes to recover the washing liquid 5 L.

The obtained washing liquid 5 L was filtered using STERICUP HV filter unit (manufactured by Millipore). The obtained filtrate was filtered through a small flat sheet membrane filtration apparatus ("Sepa" (registered trademark) CF II Med/High Foulant System manufactured by GE Osmonics) to which a flat sheet membrane of ultrafiltration membrane with a molecular weight cut off of 10000 (SEPA PW series manufactured by GE, material of functional surface: polyether sulfone) was set to separate a recovered enzyme from a sugar liquid component. As for the filtration, while an operating pressure was controlled such that the flow rate in the raw feed water side and the membrane flux were kept constant at 2.5 L/min and 0.1 m/D, 4.5 L out of 5 L was separated as a filtrate and concurrently 0.5 L was recovered as a recovered enzyme. The activity of the recovered enzyme was measured in accordance with Reference Example 1. For the sake of comparison, each enzyme activity of "Accellerase DUET" (0.8 g/L) by itself was measured in accordance with Reference Example 2; and the activity at that time was used as 100(%) to determine a relative value. The activity of cellulase and hemicellulase is summarized in Table 13 as expressed by the terms of the relative value.

Comparative Example 6

Washing of Saccharification Residues by RO Water Using the Press Filtration Apparatus, and Recovery of Enzymes from the Washing Liquid In the same procedure as described in Example 12, instead of the above-mentioned hydrothermally-treated liquid, RO water was passed and circulated in the same procedure. Further, the recovered enzyme was obtained from the washing liquid in the same procedure as described in Example 12. The recovered enzyme activity at this time is designated as 1 and shown in Table 13. For the sake of comparison, each enzyme activity of "Accellerase DUET" (0.8 g/L) by itself was measured in accordance with Reference Example 2; and the activity at that time was used as 100(%) to determine a relative value. The activity of cellulase and hemicellulase is summarized in Table 13 as expressed by the terms of the relative value.

TABLE 13

Recovered enzyme and each enzyme activity (Example 12, Comparative Example 5)

| | Avicel degrading activity (%) | Cellobiose degrading activity (%) | Xylan degrading activity (%) |
|---|---|---|---|
| Cellulase dilution liquid | 100 (standard) | 100 (standard) | 100 (standard) |
| Comparative Example 6 | 8 | 28 | 30 |
| Example 12 | 39 | 70 | 75 |

As shown in Table 13, the recovery amount of enzyme was greatly increased when the saccharification residue was washed with the hydrothermally-treated liquid (Example 12), as compared to when the same operation was carried out with RO water (Comparative Example 5).

INDUSTRIAL APPLICABILITY

The sugar liquid obtained by the method of producing a sugar liquid can be used as a fermentation raw material for various chemical substances.

The invention claimed is:
1. A method of producing a sugar liquid from cellulose-containing biomass comprising (1) to (3):
   (1): subjecting a cellulose-containing biomass to hydrothermal treatment and thereafter separating the treated cellulose-containing biomass into a hydrothermally-treated liquid and a cellulose-containing solid content;
   (2): adding a filamentous fungus-derived cellulase to the cellulose-containing solid content obtained in (1) to hydrolyze the cellulose and thereafter separating the hydrolysate into a saccharification residue and a sugar liquid; and
   (3): washing the saccharification residue obtained in the step (2) with the hydrothermally-treated liquid obtained in (1) to elute the filamentous fungus-derived cellulase adsorbed to the saccharification residue into the hydrothermally-treated liquid and thereafter obtaining a solution component comprising the filamentous fungus-derived cellulase by solid-liquid separation,
   wherein the hydrothermally-treated liquid used in the step (3) comprises enzymatic saccharification inhibitors.
2. The method according to claim 1, comprising (4) filtering the solution component obtained in (3) through an ultrafiltration membrane to thereby recover the filamentous fungus-derived cellulase as a retentate and at the same time obtain a sugar liquid as a permeate.
3. The method according to claim 2, wherein the filamentous fungus-derived cellulase recovered in (4) is reused in the cellulose hydrolysis in (2).

4. The method according to claim 1, wherein the filamentous fungus-derived cellulase is cellulase derived from *Trichoderma*.

5. The method according to claim 1, wherein the hydrothermal treatment of (1) is a treatment at 120 to 240° C.

6. The method according to claim 1, wherein the hydrothermally-treated liquid used in (3) comprises 1 g/L or more of an inorganic ion, acetic acid and/or furfural in total.

7. The method according to claim 1, wherein the saccharification residue is washed with a hydrothermally-treated liquid at 30 to 70° C. in (3).

8. The method according to claim 1, wherein (2) comprises separating the hydrolysate into a saccharification residue and a sugar liquid by membrane separation, and (3) comprises washing the saccharification residue by passing the hydrothermally-treated liquid through the saccharification residue on the surface of the membrane in a vertical direction to obtain a solution component comprising the filamentous fungus-derived cellulase.

9. The method according to claim 8, wherein the membrane separation is press filtration or membrane separation by a belt filter.

10. A method of producing a chemical substance comprising producing the sugar liquid by the method according to claim 1 and culturing a microorganism capable of producing a chemical substance using the sugar liquid as a fermentation raw material.

* * * * *